(12) United States Patent
Sugawara et al.

(10) Patent No.: US 11,643,522 B2
(45) Date of Patent: May 9, 2023

(54) POLYMER COMPOSITION CONTAINING DIARYLAMINE-BASED COMPOUND

(71) Applicant: ZEON CORPORATION, Tokyo (JP)

(72) Inventors: Mitsuru Sugawara, Tokyo (JP); Satoshi Kiriki, Tokyo (JP); Kazuhiro Ejiri, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 17/646,866

(22) Filed: Jan. 4, 2022

(65) Prior Publication Data

US 2022/0127430 A1 Apr. 28, 2022

Related U.S. Application Data

(62) Division of application No. 16/489,834, filed as application No. PCT/JP2018/006532 on Feb. 22, 2018.

(30) Foreign Application Priority Data

Mar. 3, 2017 (JP) ................. 2017-040027

(51) Int. Cl.
| | |
|---|---|
| C08K 5/3417 | (2006.01) |
| C07D 207/408 | (2006.01) |
| C07D 209/48 | (2006.01) |
| C07D 209/66 | (2006.01) |
| C07D 209/76 | (2006.01) |
| C07D 279/34 | (2006.01) |
| C08K 5/3415 | (2006.01) |
| C08K 5/46 | (2006.01) |

(52) U.S. Cl.
CPC ........ *C08K 5/3417* (2013.01); *C07D 207/408* (2013.01); *C07D 209/48* (2013.01); *C07D 209/66* (2013.01); *C07D 209/76* (2013.01); *C07D 279/34* (2013.01); *C08K 5/3415* (2013.01); *C08K 5/46* (2013.01)

(58) Field of Classification Search
CPC ..... C08K 5/005; C08K 5/3417; C07D 209/48
See application file for complete search history.

(56) References Cited

U.S. PATENT DOCUMENTS

| | | | |
|---|---|---|---|
| 3,208,939 A * | 9/1965 | Latos ..................... | C09K 15/04 44/407 |
| 3,306,852 A | 2/1967 | Hendrickson | |
| 3,699,154 A | 10/1972 | Heintzelman et al. | |
| 6,066,743 A | 5/2000 | Nick et al. | |
| 8,883,888 B2 | 11/2014 | Sakamoto et al. | |
| 2007/0142616 A1 | 6/2007 | Murray et al. | |
| 2012/0302674 A1 | 11/2012 | Ogawa et al. | |
| 2012/0302675 A1 | 11/2012 | Sakamoto et al. | |
| 2015/0087754 A1 | 3/2015 | Sakamoto et al. | |
| 2017/0119907 A1 | 5/2017 | Hung et al. | |

FOREIGN PATENT DOCUMENTS

| | | |
|---|---|---|
| DE | 951389 C2 | 10/1956 |
| EP | 0613887 A1 | 9/1994 |
| JP | 5682575 B2 | 3/2015 |
| JP | 2016117831 A * | 6/2016 |
| JP | 2017505774 A | 2/2017 |
| WO | 2004089870 A2 | 10/2004 |
| WO | 2011093443 A1 | 8/2011 |

OTHER PUBLICATIONS

Machine translation of JP 2016-117831 (2016, 8 pages).*
Farokh Mehrabani et al., Synthesis of new bis(tetrahydropyrrolo[3,4-b]carbazoles) with a functionalized diaryl spacer, Journal of the Chemical Society, Perkin Transactions 1, May 22, 2001, pp. 1406 to 1412.
H. R. Schweizer, Derivate des 5, 6-Dihydro-p-dithiin-2, 3-dicarbonsaure-anhydrids, I: Imide, Helvetica Chimica Acta, 1969, vol. 52, No. 8, pp. 2221 to 2235.
Jul. 8, 2020, the Extended European Search Report issued by the European Patent Office in the corresponding European Patent Application No. 18760244.6.
May 22, 2018, International Search Report issued in the International Patent Application No. PCT/JP2018/006532.
Mehrabani (Synthesis of new bis(tetrahydropyrrolo[3,4-b]carbazoles) with a functionalized diaryl spacer. J. Chem. Soc., Perkin Trans. 1, 2001, pp. 1406-1412).
Schweizer (Derivate des 5,6-Dihydro-p-dithiin-2,3-dicarbonsaure-anhydrids, I: Imide, Helvetica Chimica Acta, 1969, 52(8), pp. 2221-2235).
Sep. 3, 2019, International Preliminary Report on Patentability issued in the International Patent Application No. PCT/JP2018/006532.

* cited by examiner

*Primary Examiner* — Brieann R Johnston
(74) *Attorney, Agent, or Firm* — Kenja IP Law PC

(57) ABSTRACT

The present invention provides a polymer composition comprising a polymer and an antioxidant comprising a diarylamine-based compound represented by General Formula (1):

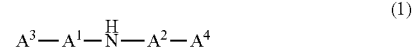

(1)

where, in General Formula (1), $A^1$ and $A^2$ each independently represent a $C_6$ to $C_{18}$ arylene group which may have a substituent, and $A^3$ and $A^4$ each independently represent an organic group having a cyclic imide structure which may have a substituent.

11 Claims, No Drawings

POLYMER COMPOSITION CONTAINING DIARYLAMINE-BASED COMPOUND

CROSS-REFERENCE TO RELATED APPLICATIONS

The present application is a divisional application of U.S. patent application Ser. No. 16/489,834 filed Aug. 29, 2019, which is a National Stage Application of PCT/JP2018/006532 filed Feb. 22, 2018, which claims priority of Japanese Patent Application No. 2017-040027 filed Mar. 3, 2017. The disclosures of the prior applications are hereby incorporated by reference herein in their entirety.

TECHNICAL FIELD

The disclosure relates to a novel diarylamine-based compound which has an excellent antioxidant effect on polymer materials required to have high heat resistance (for example, heat resistance in a high temperature range of 190° C. or more) and can be suitably used as an antioxidant, and an antioxidant and a polymer composition comprising such a diarylamine-based compound.

BACKGROUND ART

With development of petrochemistry, polymers composed of organic compounds have contributed to human development in a variety of forms such as plastics, rubber, fibers, and films. Because these polymers are used in a variety of environments according to their applications, improvements so as to allow long-term use thereof have been made by imparting, to each polymer, a durability under an environment expected for the polymer. For example, products have been developed by imparting UV resistance to plastics to be used outdoors and cold resistance to rubber which functions even in extremely cold regions.

On the other hand, internal combustion engines, such as engines, which have been increasingly used with industrial development, need lubricant oil and generate an enormous amount of heat. For this reason, polymers used in those internal combustion engines should have resistances against oil and high temperature. In particular, polymers used in automobile engines are required to have properties such that even after exposed to oil and high temperature, they can maintain flexibility for a long time without generating defects such as cracks. To satisfy such a demand, a variety of oil-resistant and heat-resistant rubbers have been developed. Among these, acrylic rubber, which is a group of polymers having rubber elasticity and having high oil resistance, heat resistance, and flexibility, is widely used as members used in automobile engines, e.g., seals, gaskets, packings, and hoses. According to the properties to be required, the oil resistance and the heat resistance are further enhanced by designing cross-linked structures, antioxidants, compounding agents, and the like.

For example, Patent Document 1 discloses an antioxidant which improves heat resistance. Unfortunately, while the antioxidant disclosed in Patent Document 1 has a sufficient ability to prevent degradation attributed to alteration after long-term use, which is caused by oxidation or the like of a functional group of a monomer unit which forms a polymer, the antioxidant has a poor ability to prevent degradation attributed to a reduction in molecular weight, which is caused by scission of molecular chains at the initial state of thermal degradation. For this reason, in some cases, sufficient heat resistance in a high temperature range of 190° C. or more is not achieved, and a further requirement on heat resistance in these days is insufficiently satisfied.

RELATED ART

Patent Document

Patent Document 1: Japanese Patent No. 5682575

SUMMARY OF THE INVENTION

Technical Problem

The present invention has been made in consideration of such circumstances described above. An object of the present invention is to provide a novel diarylamine-based compound which has an excellent antioxidant effect on polymer materials required to have high heat resistance (for example, heat resistance in a high temperature range of 190° C. or more), and is suitable as an antioxidant, and an antioxidant and a polymer composition containing the diarylamine-based compound.

Solution to Problem

The present inventors, who have conducted extensive research to achieve the object above, have found a novel diarylamine-based compound which can impart high thermal stability and the like to polymer materials.

In other words, one aspect of the present invention provides a diarylamine-based compound represented by General Formula (1):

(1)

where, in the General Formula (1), $A^1$ and $A^2$ each independently represent a $C_6$ to $C_{18}$ arylene group which may have a substituent, and $A^3$ and $A^4$ each independently represent an organic group having a cyclic imide structure which may have a substituent.

In the diarylamine-based compound according to one aspect of the present invention, it is preferred that $A^3$ and $A^4$ each independently be an organic group represented by General Formula (2) or (3), and it is more preferred that $A^3$ and $A^4$ each independently be any of organic groups represented by General Formulae (4) to (9):

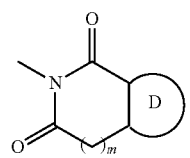

(2)

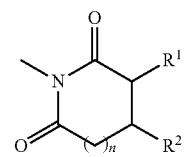

(3)

where, in the General Formula (2), D represents a $C_6$ to $C_{18}$ ring which may have a substituent, and "m" represents 0 or 1. In General Formula (3), $R^1$ and $R^2$ each independently represent a hydrogen atom, a $C_1$ to $C_{30}$ alkyl group which may have a substituent, or a $C_1$ to $C_{30}$ alkenyl group which may have a substituent, and "n" represents 0 or 1.

The diarylamine-based compound according to one aspect of the present invention is preferably any of compounds represented by General Formulae (10) to (13), more preferably any of compounds represented by General Formulae (14) to (18):

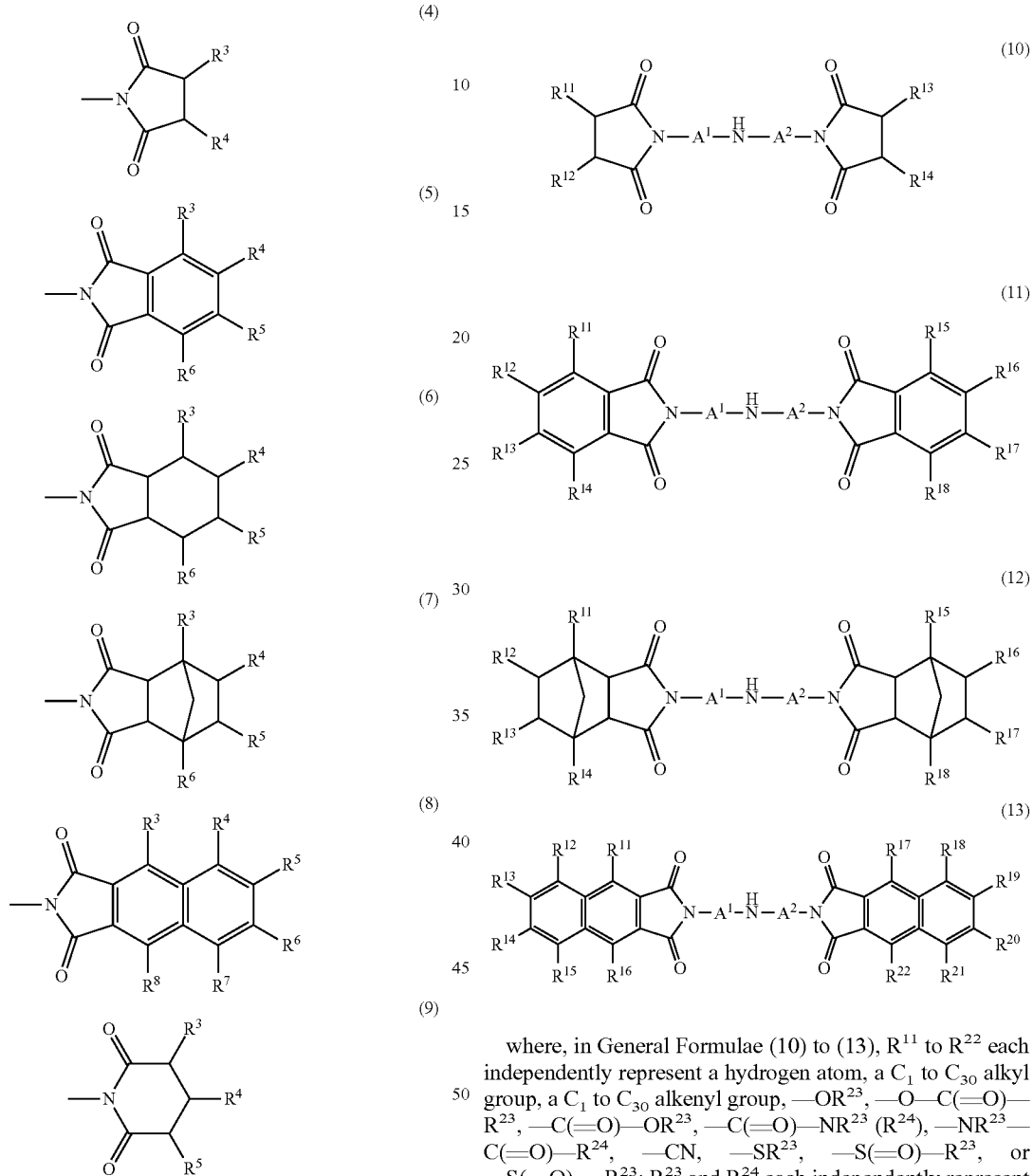

where, in General Formulae (4) to (9), $R^3$ to $R^8$ each independently represent a hydrogen atom, a $C_1$ to $C_{30}$ alkyl group, a $C_1$ to $C_{30}$ alkenyl group, —O—$R^9$, —O—C(=O)—$R^9$, —C(=O)—O—$R^9$, —C(=O)—N$R^9$($R^{10}$), —N$R^9$—C(=O)—$R^{10}$, —CN, —S$R^9$, —S(=O)—$R^9$, or —S(=O)$_2$—$R^9$; $R^9$ and $R^{10}$ each independently represent a $C_1$ to $C_{30}$ alkyl group, a $C_1$ to $C_{30}$ alkenyl group, or a $C_6$ to $C_{12}$ aromatic group. When two or more $R^3$ to $R^8$ are present, these may be the same or may be different.

In the diarylamine-based compound according to one aspect of the present invention, $A^1$ and $A^2$ are preferably a 1,4-phenylene group.

where, in General Formulae (10) to (13), $R^{11}$ to $R^{22}$ each independently represent a hydrogen atom, a $C_1$ to $C_{30}$ alkyl group, a $C_1$ to $C_{30}$ alkenyl group, —O$R^{23}$, —O—C(=O)—$R^{23}$, —C(=O)—O$R^{23}$, —C(=O)—N$R^{23}$($R^{24}$), —N$R^{23}$—C(=O)—$R^{24}$, —CN, —S$R^{23}$, —S(=O)—$R^{23}$, or —S(=O)$_2$—$R^{23}$; $R^{23}$ and $R^{24}$ each independently represent a $C_1$ to $C_{30}$ alkyl group, a $C_1$ to $C_{30}$ alkenyl group, or a $C_6$ to $C_{12}$ aromatic group; and $A^1$ and $A^2$ are the same as those in General Formula (1) above.

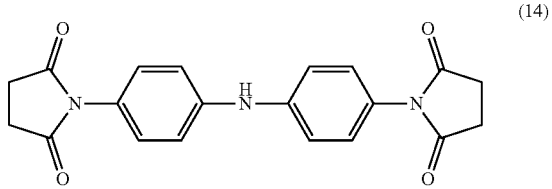

-continued (15)

(16)

(17)

(18)

One aspect of the present invention also provides a composition comprising the diarylamine-based compound and a condensed heterocyclic compound represented by General Formula (19):

(19)

where, in the formula, $Y^1$ represents a chemical single bond, —S(=O)—, or —SO$_2$—;

$R^a$ and $R^b$ each independently represent a $C_1$ to $C_{30}$ organic group which may have a substituent;

$Z^a$ and $Z^b$ each independently represent a chemical single bond or —SO$_2$—;

$X^1$ and $X^2$ each independently represent a hydrogen atom, a halogen atom, a $C_1$ to $C_{10}$ alkyl group which may have a substituent, a cyano group, a nitro group, —OR$^{25}$, —O—C(=O)—R$^{25}$, —C(=O)—OR$^{25}$, —O—C(=O)—OR$^{25}$, —NR$^{26}$ (R$^{27}$), —NR$^{26}$—C(=O)—R$^{25}$, —C(=O)—NR$^{26}$ (R$^{27}$), or —O—C(=O)—NR$^{26}$ (R$^{27}$), where R$^{25}$, R$^{26}$, and R$^{27}$ each independently represent a hydrogen atom or a $C_1$ to $C_{20}$ organic group which may have a substituent;

"n" and "m" each independently represent an integer of 0 to 2, and one of "n" and "m" is not 0; and when "n" and/or "m" is 2, two $R^a$ and two $R^b$ each may be the same or may be different.

In the composition according to one aspect of the present invention, it is preferred that $R^a$ and $R^b$ each independently represent a linear or branched $C_1$ to $C_{20}$ alkyl group which may have a substituent, or a phenyl group which may have a substituent.

In the composition according to one aspect of the present invention, the condensed heterocyclic compound represented by General Formula (19) above is preferably a compound represented by General Formula (20) or (21):

(20)

(21)

In the composition according to one aspect of the present invention, the weight ratio of the diarylamine-based compound to the condensed heterocyclic compound, i.e., "diarylamine-based compound:condensed heterocyclic compound" is preferably 30:1 to 1:30.

Furthermore, one aspect of the present invention provides an antioxidant comprising the diarylamine-based compound or the composition.

The antioxidant according to one aspect of the present invention is preferably an antioxidant for a polymer.

One aspect of the present invention also provides a polymer composition comprising a polymer and the antioxidant.

In the polymer composition according to one aspect of the present invention, the polymer is preferably a synthetic resin or a rubber. Among rubbers, an acrylic rubber is preferred.

In the polymer composition according to one aspect of the present invention, the content of the antioxidant is preferably 0.05 to 30 parts by weight relative to 100 parts by weight of the polymer.

Advantageous Effects

One aspect of the present invention can provide a novel diarylamine-based compound which has an excellent antioxidant effect on polymer materials required to have high heat resistance (for example, heat resistance in a high temperature range of 190° C. or more) and can be suitably used as an antioxidant, and an antioxidant and a polymer composition comprising such a diarylamine-based compound.

DESCRIPTION OF EMBODIMENTS

<Diarylamine-Based Compound>

The diarylamine-based compound according to one embodiment of the present invention is a compound represented by General Formula (1) below. The compound has an excellent antioxidant effect on polymer materials required to have high heat resistance, and is suitable as an antioxidant.

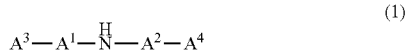
(1)

In General Formula (1), $A^1$ and $A^2$ each independently represent a $C_6$ to $C_{18}$ arylene group which may have a substituent, and $A^3$ and $A^4$ each independently represent an organic group having a cyclic imide structure which may have a substituent.

In particular, the present inventors, who have conducted extensive research, have found the followings: According to the diarylamine-based compound according to one embodiment of the present invention, the structure represented by General Formula (1) above can effectively prevent degradation of polymer materials attributed to a reduction in molecular weight, which is caused by scission of the molecular chains at the initial state of thermal degradation. Furthermore, as shown in the structure represented by General Formula (1), an imide structure bonded to both sides of a diarylamine can enhance the heat resistance of the diarylamine-based compound itself. This can prevent decomposition of the diarylamine-based compound itself even in a degradation temperature range (for example, heat resistance in a high temperature range of 190° C. or more), for example, so that the diarylamine-based compound itself can be appropriately present in a system even in a severe degradation environment. Thus, its degradation preventing effect can persist favorably for a long time. Based on these findings, the present inventors have completed one embodiment of the present invention. The diarylamine-based compound according to one embodiment of the present invention can also be relatively easily synthesized, which leads to industrial advantages.

In General Formula (1), $A^1$ and $A^2$ each independently are a $C_6$ to $C_{18}$ arylene group which may have a substituent, preferably a $C_6$ to $C_{10}$ arylene group which may have a substituent, more preferably a phenylene group which may have a substituent, still more preferably a 1,4-phenylene group. In particular, to attain a better antioxidant effect, it is particularly preferred that both of $A^1$ and $A^2$ be a 1,4-phenylene group. Examples of the substituent include halogen atoms such as fluorine, chlorine, and bromine atoms; $C_1$ to $C_{10}$ alkoxy groups such as a methoxy group, an ethoxy group, and an isopropoxy group; a nitro group; a cyano group; $C_1$ to $C_{10}$ alkyl groups such as a methyl group, an ethyl group, and a t-butyl group; and the like.

In General Formula (1) above, $A^3$ and $A^4$ each independently are an organic group having a cyclic imide structure which may have a substituent, and are preferably an organic group represented by General Formula (2) or (3):

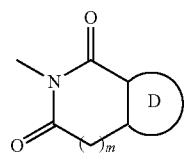
(2)

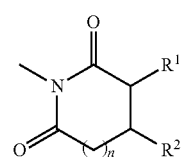
(3)

In General Formula (2), D represents a $C_6$ to $C_{18}$ ring which may have a substituent, preferably a $C_6$ to $C_{10}$ ring which may have a substituent; and D may be monocyclic or polycyclic. Examples of the substituent in this case include $C_1$ to $C_{30}$ alkyl groups, $C_1$ to $C_{30}$ alkenyl groups, —O—$R^{28}$, —O—C(=O)—$R^{28}$, —C(=O)—O—$R^{28}$, —C(=O)—$NR^{28}$($R^{29}$), —$NR^{28}$—C(=O)—$R^{29}$, —CN, —$SR^{28}$, —S(=O)—$R^{28}$, —S(=O)$_2$—$R^{28}$, and the like. $R^{28}$ and $R^{29}$ each independently represent a $C_1$ to $C_{30}$ alkyl group, a $C_1$ to $C_{30}$ alkenyl group, or a $C_6$ to $C_{12}$ aromatic group. "m" represents 0 or 1, and preferably is 0.

In General Formula (3), $R^1$ and $R^2$ each independently represent a hydrogen atom, a $C_1$ to $C_{30}$ alkyl group which may have a substituent, or a $C_1$ to $C_{30}$ alkenyl group which may have a substituent. Preferred is a hydrogen atom or a $C_1$ to $C_{20}$ alkyl group which may have a substituent, and more preferred is a hydrogen atom or a $C_1$ to $C_{10}$ alkyl group which may have a substituent. Examples of the substituent in this case include halogen atoms, such as fluorine, chlorine, and bromine atoms; $C_1$ to $C_{10}$ alkoxy groups, such as a methoxy group, an ethoxy group, and an isopropoxy group; a nitro group; a cyano group; phenyl groups which may have a substituent, such as a phenyl group, a 4-methylphenyl group, and a 2-chlorophenyl group; and the like. "n" represents 0 or 1, and preferably is 0.

Among these organic groups forming $A^3$ and $A^4$, which are represented by General Formulae (2) and (3), preferred are any of organic groups represented by General Formulae (4) to (9) to attain a better antioxidant effect:

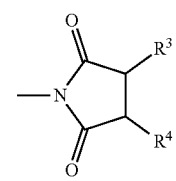
(4)

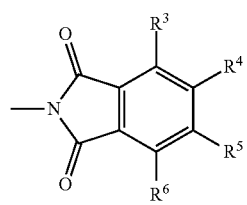
(5)

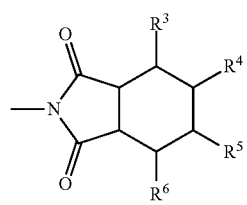
(6)

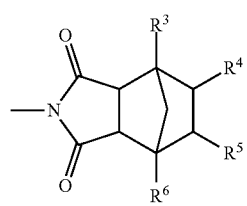
(7)

(8)

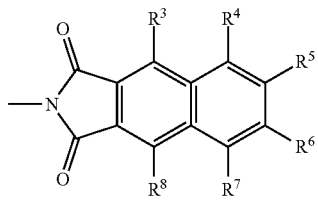

(9)

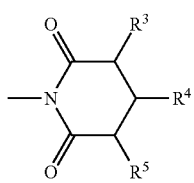

In General Formulae (4) to (9), $R^3$ to $R^8$ each independently represent a hydrogen atom, a $C_1$ to $C_{30}$ alkyl group, a $C_1$ to $C_{30}$ alkenyl group, —O—$R^9$, —O—C(=O)—$R^9$, —C(=O)—O—$R^9$, —C(=O)—$NR^9$ ($R^{10}$), —$NR^9$—C(=O)—$R^{10}$, —CN, —$SR^9$, —S(=O)—$R^9$, or —S(=O)$_2$—$R^9$; and $R^9$ and $R^{10}$ each independently represent a $C_1$ to $C_{30}$ alkyl group, a $C_1$ to $C_{30}$ alkenyl group, or a $C_6$ to $C_{12}$ aromatic group. It is preferred that $R^3$ to $R^8$ each independently be a hydrogen atom or a $C_1$ to $C_{30}$ alkyl group. More preferred is a hydrogen atom or a $C_1$ to $C_{20}$ alkyl group. Particularly preferred is a hydrogen atom or a $C_1$ to $C_{10}$ alkyl group. When two or more $R^3$ to $R^8$ are present, these may be the same or may be different.

Among these organic groups represented by General Formulae (4) to (9) above, more preferred is an organic group represented by General Formula (4), (5), (7), or (8), still more preferred is an organic group represented by General Formula (4), (5), or (8), and particularly preferred is an organic group represented by General Formula (5) to further enhance the antioxidant effect.

The diarylamine-based compound according to one embodiment of the present invention is preferably one of compounds represented by General Formulae (10) to (13):

(10)

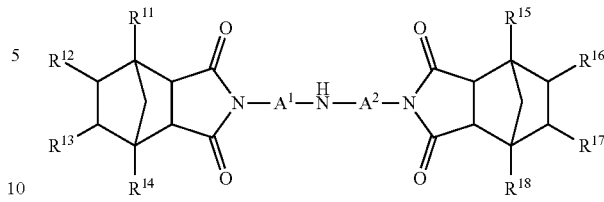

(11)

(12)

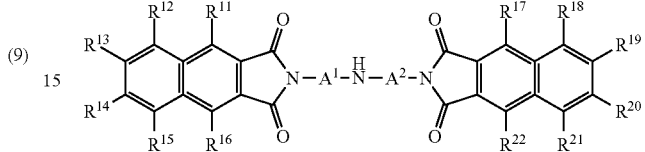

(13)

In General Formulae (10) to (13), $R^{11}$ to $R^{22}$ each independently represent a hydrogen atom, a $C_1$ to $C_{30}$ alkyl group, a $C_1$ to $C_{30}$ alkenyl group, —$OR^{23}$, —O—C(=O)—$R^{23}$, —C(=O)—$OR^{23}$, —C(=O)—$NR^{23}$ ($R^{24}$), —$NR^{23}$—C(=O)—$R^{24}$, —CN, —$SR^{23}$, —S(=O)—$R^{23}$, or —S(=O)$_2$—$R^{23}$; and $R^{23}$ and $R^{24}$ each independently represent a $C_1$ to $C_{30}$ alkyl group, a $C_1$ to $C_{30}$ alkenyl group, or a $C_6$ to $C_{12}$ aromatic group. It is preferred that $R^{11}$ to $R^{22}$ each independently be a hydrogen atom or a $C_1$ to $C_{30}$ alkyl group. More preferred is a hydrogen atom or a $C_1$ to $C_{20}$ alkyl group. Particularly preferred is a hydrogen atom or a $C_1$ to $C_{10}$ alkyl group. $A^1$ and $A^2$ are the same as those in General Formula (1) above.

Among these compounds represented by General Formulae (10) to (13), particularly preferred are compounds represented by General Formula (11) to further enhance the antioxidant effect.

The diarylamine-based compound according to one embodiment of the present invention can be prepared by any synthetic method. The diarylamine-based compound according to one embodiment of the present invention can be relatively easily synthesized, for example, by a synthetic method of reacting a diamine compound represented by General Formula (22) below with its corresponding dicarboxylic anhydride in an organic solvent by heating under reflux to form an imide ring.

(22)

(where $A^1$ and $A^2$ are the same as those in General Formula (1) above).

In the case where a compound is prepared where $A^3$ and $A^4$ in General Formula (1) are an organic group represented by General Formula (2) or (3) above, the dicarboxylic anhydride to be used can be a compound represented by General Formula (23) or (24):

(23)

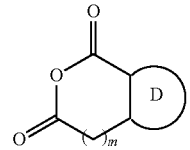

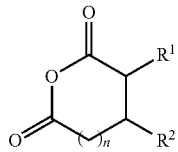

(where D, $R^1$, $R^2$, m, and n are the same as those in General Formulae (2) and (3) above).

For example, synthesis of a compound represented by General Formula (10) above where $R^{11}$, $R^{12}$, $R^{13}$, and $R^{14}$ all are a hydrogen atom (such a compound is represented by General Formula (10a) in the scheme below) is exemplified. The synthesis reaction is as shown below:

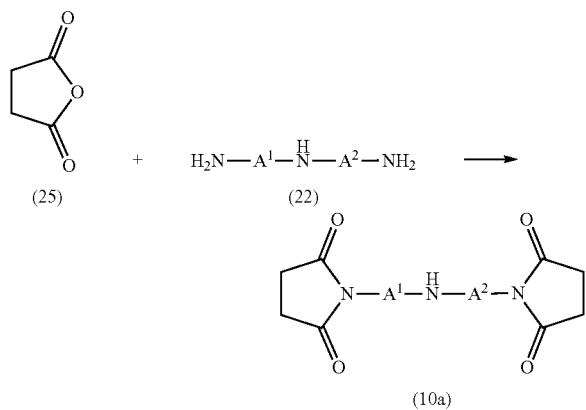

The reaction temperature for the reaction above is preferably −30 to 250° C., more preferably 0 to 200° C. In this reaction, one molecule of a compound represented by General Formula (22) above should be reacted with two molecules of a compound represented by General Formula (25) above. Thus, the amounts of these compounds to be used are determined according to this ratio.

Examples of the organic solvent include apolar solvents such as apolar ether solvents such as 1,2-dimethoxyethane, 1,4-dioxane, and tetrahydrofuran (THF), and apolar aromatic hydrocarbon solvents such as benzene, toluene, and xylene; aprotic polar solvents such as nitrogen-containing aprotic polar solvents such as N,N-dimethylformamide (DMF), N,N-dimethylacetamide, hexamethylphosphoric triamide, and N-methylpyrrolidinone (NMP), aprotic polar ketone solvents such as acetone, methyl ethyl ketone (MEK), and methyl isobutyl ketone (MIBK), and aprotic polar ester solvents such as ethyl acetate and butyl acetate; and the like.

The reaction above is usually performed in the presence of an acid or base catalyst. Examples of acids to be used as the acid catalyst include, but should not be limited to, inorganic acids such as hydrochloric acid, sulfuric acid, and phosphoric acid; and organic acids such as p-toluenesulfonic acid, 10-camphorsulfonic acid, and acetic acid. Examples of bases to be used as the base catalyst include, but should not be limited to, tertiary amines such as triethylamine, diisopropylethylamine, and N-methylmorpholine; pyridines such as pyridine, picoline, lutidine, and 4-(dimethylamino)pyridine; and inorganic bases such as sodium hydroxide, potassium hydroxide, and potassium carbonate.

In the reaction above, the target product is precipitated in the reaction solution as the reaction proceeds. After the reaction is completed, the target product is precipitated by cooling the reaction solution, and adding a poor solvent which does not dissolve the target product. Thus, the diarylamine-based compound according to one embodiment of the present invention can be yielded. Examples of the poor solvent include $C_1$ to $C_5$ lower alcohols such as methanol, and the like. In particular, because bases, which are byproducts, can be dissolved by adding a poor solvent such as methanol, a substantially impurity-free diarylamine-based compound according to one embodiment of the present invention as the target product can be obtained. For this reason, the diarylamine-based compound according to one embodiment of the present invention can be isolated with a high yield only through a simple operation, i.e., filtration of the reaction solution. The structure of the resulting compound can be identified by measurement of a spectrum such as an NMR spectrum, an IR spectrum, or a mass spectrum and/or elemental analysis.

Because the diarylamine-based compound according to one embodiment of the present invention has an excellent antioxidant effect on polymer materials required to have high heat resistance (for example, heat resistance in a high temperature range of 190° C. or more), the compound is suitably used as an antioxidant, and especially, is particularly suitably used as an antioxidant for polymers. In particular, the diarylamine-based compound according to one embodiment of the present invention can effectively prevent degradation attributed to a reduction in molecular weight, which is caused by scission of molecular chains at the initial state of thermal degradation of polymer materials. Furthermore, because of its high heat resistance, the degradation preventing effect can persist favorably for a long time. Accordingly, the diarylamine-based compound according to one embodiment of the present invention is suitably used as an antioxidant, especially, as an antioxidant for polymers. If the diarylamine-based compound according to one embodiment of the present invention is used as an antioxidant, an antioxidant other than the diarylamine-based compound according to one embodiment of the present invention (such as a known antioxidant in the related art or the like) may be appropriately used in combination in the range not impairing the object and effects of one embodiment of the present invention.

<Composition>

The composition according to one embodiment of the present invention comprises the diarylamine-based compound represented by General Formula (1) and a condensed heterocyclic compound represented by General Formula (19) below. According to the composition according to one embodiment of the present invention, the antioxidant effect can be further enhanced by adding the condensed heterocyclic compound represented by General Formula (19) to the diarylamine-based compound represented by General Formula (1) described above. In particular, the condensed heterocyclic compound represented by General Formula (19) has a high ability to prevent degradation attributed to oxidation of a polymer after long-term use. Because of such properties, use of the condensed heterocyclic compound represented by General Formula (19) below in combination can further enhance the antioxidant effect:

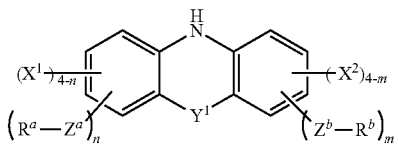

(19)

where $Y^1$ represents a chemical single bond, —S(=O)—, or —SO$_2$—; preferred are —S(=O)— and —SO$_2$—, and more preferred is —SO$_2$—.

In General Formula (19) above, $R^a$ and $R^b$ each independently represent a $C_1$ to $C_{30}$ organic group which may have a substituent.

Examples of the $C_1$ to $C_{30}$ organic group forming $R^a$ and $R^b$ include $C_1$ to $C_{30}$ alkyl groups such as a methyl group, an ethyl group, an n-propyl group, an isopropyl group, an n-butyl group, an isobutyl group, a sec-butyl group, a t-butyl group, an n-pentyl group, an n-hexyl group, an n-heptyl group, an n-octyl group, an n-nonyl group, and an n-decyl group; $C_3$ to $C_{30}$ cycloalkyl groups such as a cyclopropyl group, a cyclopentyl group, a cyclohexyl group, a cycloheptyl group, and a cyclooctyl group; $C_6$ to $C_{30}$ aryl groups such as a phenyl group, a biphenyl group, a naphthyl group, and an anthranil group; $C_1$ to $C_{30}$ alkoxy groups such as a methoxy group, an ethoxy group, an n-propoxy group, an isopropoxy group, an n-butoxy group, an isobutoxy group, a sec-butoxy group, a t-butoxy group, an n-pentyloxy group, and an n-hexyloxy group; and the like.

The organic group forming $R^a$ and $R^b$ described above may have a substituent at any position.

When the organic group is an alkyl group, examples of a substituent for the organic group include halogen atoms such as fluorine, chlorine, and bromine atoms; $C_1$ to $C_{10}$ alkoxy groups such as a methoxy group, an ethoxy group, and an isopropoxy group; a nitro group; a cyano group; phenyl groups which may have a substituent, such as a phenyl group, a 4-methylphenyl group, and a 2-chlorophenyl group; and the like.

When the organic group is a cycloalkyl group or an aryl group, examples thereof include halogen atoms such as fluorine, chlorine, and bromine atoms; $C_1$ to $C_{10}$ alkoxy groups such as a methoxy group, an ethoxy group, and an isopropoxy group; a nitro group; a cyano group; $C_1$ to $C_{10}$ alkyl groups such as a methyl group, an ethyl group, and a t-butyl group; and the like.

When the organic group is an alkoxy group, examples thereof include halogen atoms such as fluorine, chlorine, and bromine atoms; a nitro group; a cyano group; and the like.

When the organic group forming $R^a$ and $R^b$ has a substituent, the carbon atoms of the substituent are not counted as carbon atoms of the organic group. In other words, the number of carbon atoms of the organic group forming $R^a$ and $R^b$ is in the range of 1 to 30 excluding the carbon atoms contained in the substituent. For example, when the organic group forming $R^a$ and $R^b$ is a methoxyethyl group, the organic group has two carbon atoms. In other words, because the methoxy group is a substituent in this case, the number of carbon atoms of the organic group corresponds to that excluding the carbon atom of the methoxy group as the substituent.

In one embodiment of the present invention, it is preferred that $R^a$ and $R^b$ each independently be a linear or branched $C_1$ to $C_{20}$ alkyl group which may have a substituent, a phenyl group which may have a substituent, or a naphthyl group which may have a substituent. More preferred is a linear or branched $C_2$ to $C_8$ alkyl group which may have a substituent or a phenyl group which may have a substituent.

Preferred specific examples of the organic group forming $R^a$ and $R^b$ described above include an α-methylbenzyl group, an α,α-dimethylbenzyl group, a t-butyl group, a phenyl group, and a 4-methylphenyl group, and the like. Among these groups, particularly preferred is an α,α-dimethylbenzyl group or a 4-methylphenyl group. $R^a$ and $R^b$ can each be independent.

In General Formula (19), $Z^a$ and $Z^b$ each independently are a chemical single bond or —SO$_2$—. Preferred is a chemical single bond.

In General Formula (19), $X^1$ and $X^2$ each independently represent a hydrogen atom, a halogen atom, a $C_1$ to $C_{10}$ alkyl group which may have a substituent, a cyano group, a nitro group, —OR$^{25}$, —O—C(=O)—R$^{25}$, —C(=O)—OR$^{25}$, —O—C(=O)—OR$^{25}$, —NR$^{26}$(R$^{27}$), —NR$^{26}$—C(=O)—R$^{25}$, —C(=O)—NR$^{26}$(R$^{27}$), or —O—C(=O)—NR$^{26}$(R$^{27}$).

Examples of the halogen atom forming $X^1$ and $X^2$ include fluorine, chlorine, bromine atoms, and the like.

Examples of $C_1$ to $C_{10}$ alkyl groups for the $C_1$ to $C_{10}$ alkyl group which may have a substituent include a methyl group, an ethyl group, a propyl group, an isopropyl group, an n-butyl group, an isobutyl group, a t-butyl group, an n-pentyl group, an n-hexyl group, an n-heptyl group, an n-octyl group, an n-nonyl group, an n-decyl group, and the like.

Examples of the substituent for the $C_1$ to $C_{10}$ alkyl group include halogen atoms such as fluorine, chlorine, and bromine atoms; alkoxy groups such as a methoxy group, an ethoxy group, an n-propoxy group, an isopropoxy group, an n-butoxy group, and a t-butoxy group; a nitro group; a cyano group; and the like.

$R^{25}$, $R^{26}$, and $R^{27}$ each independently represent a hydrogen atom or a $C_1$ to $C_{20}$ organic group which may have a substituent, and it is preferred that $R^{25}$, $R^{26}$ and $R^{27}$ all be a hydrogen atom.

Examples of $C_1$ to $C_{20}$ organic groups for the $C_1$ to $C_{20}$ organic group which forms $R^{25}$, $R^{26}$, and $R^{27}$ and may have a substituent include $C_1$ to $C_{20}$ alkyl groups such as a methyl group, an ethyl group, an n-propyl group, an isopropyl group, an n-butyl group, an isobutyl group, a t-butyl group, an n-pentyl group, an n-hexyl group, an n-heptyl group, an n-octyl group, an n-nonyl group, and an n-decyl group; $C_3$ to $C_{20}$ cycloalkyl groups such as a cyclopropyl group, a cyclopentyl group, a cyclohexyl group, a cycloheptyl group, and a cyclooctyl group; $C_6$ to $C_{20}$ aryl groups such as a phenyl group, a naphthyl group, and an anthranil group; $C_1$ to $C_{20}$ alkoxy groups such as a methoxy group, an ethoxy group, an n-propoxy group, an isopropoxy group, an n-butoxy group, an isobutoxy group, a sec-butoxy group, a t-butoxy group, an n-pentyloxy group, and an n-hexyloxy group; and the like.

Examples of the substituent for the organic group forming $R^{25}$, $R^{26}$, and $R^{27}$ include the same substituents as those listed above as the substituents for the organic group forming $R^a$ and $R^b$.

Among these, $X^1$ and $X^2$ both are preferably a hydrogen atom from the viewpoint of availability.

In General Formula (19), "n" and "m" each independently represent an integer of 0 to 2, and one of "n" and "m" is not 0. It is preferred that "n" and "m" each independently be 0 or 1 (where one of "n" and "m" is not 0), and it is more preferred that "n" and "m" be 1.

When "n" and/or "m" is 2, two $R^a$ and two $R^b$ each may be the same or different.

The condensed heterocyclic compound used in one embodiment of the present invention is preferably any of compounds represented by General Formulae (26) to (33):

(26)
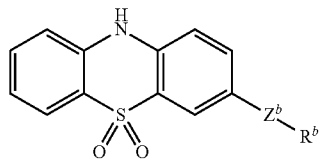

(27)
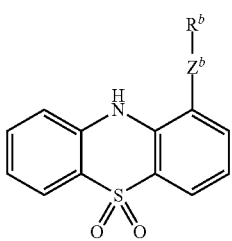

(28)
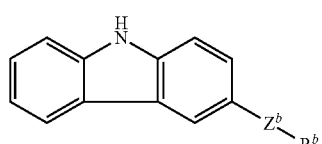

(29)
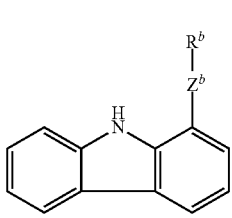

(30)
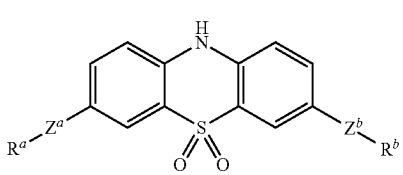

(31)
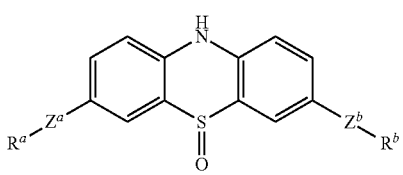

(32)
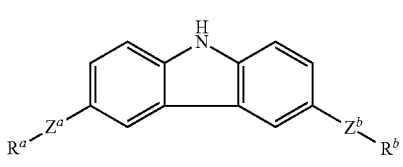

(33)
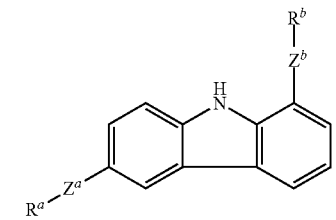

(where $R^a$, $R^b$, $Z^a$, and $Z^b$ are the same as those described in General Formula (19)).

Among these compounds represented by General Formulae (26) to (33), more preferred are compounds represented by General Formulae (26), (30), and (31). Still more preferred are compounds represented by General Formulae (30) and (31). Particularly preferred are compounds represented by General Formula (31).

In General Formulae (26) to (33), more preferred are compounds where $-Z^a-R^a$ and $-Z^b-R^b$ each independently be an α-methylbenzyl group, an α,α-dimethylbenzyl group, a t-butyl group, a phenylsulfonyl group, or a 4-methylphenylsulfonyl group. Particularly preferred are compounds where $-Z^a-R^a$ and $-Z^b-R^b$ each independently be an α,α-dimethylbenzyl group.

Compounds represented by General Formula (19) above can be synthesized by a process described in WO 2011/093443. For example, among the compounds represented by General Formula (19) above, a compound where $Y^1$ is $-S(=O)-$ and a compound where $Y^1$ is $-SO_2-$ can be prepared by preparing a compound where $Y^1$ in General Formula (19) is S by a known process of preparing a phenothiazine compound, and then oxidizing the compound. Among the compounds represented by General Formula (19), a compound where $Y^1$ is a single bond can be prepared by a known process of preparing a carbazole compound.

The diarylamine-based compound represented by General Formula (1) and the condensed heterocyclic compound represented by General Formula (19) are contained in the composition according to one embodiment of the present invention in a weight ratio of "the diarylamine-based compound represented by General Formula (1) to the condensed heterocyclic compound represented by General Formula (19)" of preferably 30:1 to 1:30, more preferably 15:1 to 1:5, still more preferably 8:1 to 1:1.

Because the composition according to one embodiment of the present invention comprises the diarylamine-based compound represented by General Formula (1) and the condensed heterocyclic compound represented by General Formula (19), the composition has an excellent antioxidant effect on polymer materials required to have high heat resistance (for example, heat resistance in a high temperature range of 190° C. or more). For this reason, the composition is suitably used as an antioxidant, and especially, is particularly suitably used as an antioxidant for polymers. In the case where the composition according to one embodiment of the present invention is used as an antioxidant, an additional antioxidant (e.g., a known antioxidant in the related art or the like) other than the diarylamine-based compound represented by General Formula (1) and the condensed heterocyclic compound represented by General Formula (19) may be appropriately used in combination in the range not impairing the object and effects of one embodiment of the present invention.

<Polymer Composition>

The polymer composition according to one embodiment of the present invention comprises a polymer and, as an antioxidant, the diarylamine-based compound represented by General Formula (1) or a composition comprising the diarylamine-based compound represented by General Formula (1) and the condensed heterocyclic compound represented by General Formula (19).

Examples of the polymer used in one embodiment of the present invention include synthetic resins and rubbers. Any synthetic resin used in applications where heat resistance is required can be used without limitation. Examples thereof include polyolefins, polystyrene resins, polyesters, polycarbonates, polyamides, and the like. These synthetic resins can be used alone or in combination.

Any rubber used in applications where heat resistance is required can be used without limitation. Examples thereof include rubbers having a conjugated diene unit such as natural rubber, isoprene rubber, butadiene rubber, butyl rubber, chloroprene rubber, styrene-butadiene copolymer rubber, acrylonitrile-butadiene copolymer rubber (nitrile rubber), styrene-butadiene-isoprene copolymer rubber, butadiene-isoprene copolymer rubber, and acrylonitrile-styrene-butadiene copolymer rubber; acrylic rubber; epichlorohydrin rubber; ethylene propylene rubber; and the like. These rubbers may have a hydroxyl group, a carboxyl group, an alkoxysilyl group, an amino group, an epoxy group, or the like. These rubbers may be hydrogenated. Examples thereof include hydrogenated products of acrylonitrile-butadiene copolymer rubber (hydrogenated nitrile rubber). These rubbers may be used alone or in combination. Furthermore, these rubbers may be used in combination with the synthetic resins described above. Among these rubbers, particularly, acrylic rubber or hydrogenated nitrile rubber, which are required to have high heat resistance, is preferred because a high effect to improve their heat resistance can be obtained. Acrylic rubber is particularly preferred.

As an antioxidant, the diarylamine-based compound represented by General Formula (1) or the composition comprising the diarylamine-based compound represented by General Formula (1) and the condensed heterocyclic compound represented by General Formula (19) can be compounded with the polymer by any method. Examples thereof include a method of compounding the antioxidant with a polymer latex or a polymer solution, a process of coagulating a polymer latex or a polymer solution to deposit the polymer, and then compounding the antioxidant with the polymer in any step later. For example, the antioxidant may be compounded in a stage of preparing polymer pellets, in a stage of compounding and kneading a variety of compounding agents, or in a stage of forming using a forming apparatus. The timing of compounding may be appropriately selected so as to sufficiently homogeneously disperse the antioxidant in the polymer.

The compounding amount of the antioxidant, i.e., the diarylamine-based compound represented by General Formula (1) or the composition comprising the diarylamine-based compound represented by General Formula (1) and the condensed heterocyclic compound represented by General Formula (19) is preferably 0.05 to 30 parts by weight, more preferably 0.1 to 15 parts by weight, still more preferably 0.3 to 10 parts by weight, particularly preferably 0.6 to 6 parts by weight relative to 100 parts by weight of the polymer. A compounding amount within this range can provide a sufficient antioxidant effect while preventing bleeding or discoloring of final products.

In the polymer composition according to one embodiment of the present invention, an additional antioxidant (e.g., a known antioxidant in the related art or the like) other than the diarylamine-based compound represented by General Formula (1) or the composition comprising the diarylamine-based compound represented by General Formula (1) and the condensed heterocyclic compound represented by General Formula (19) may be appropriately used in the range not impairing the object and effects of one embodiment of the present invention. In this case, the total compounding amount of all the antioxidants including such an additional antioxidant preferably falls within this range.

<Acrylic Rubber>

An acrylic rubber, as one example of the polymer constituting the polymer composition according to one embodiment of the present invention, is a rubber comprising 50 to 100% by weight of a (meth)acrylic acid ester monomer unit, 10 to 0% by weight of a cross-linkable monomer unit, and 50 to 0% by weight of an additional monomer unit copolymerizable with monomers which form these monomer units, as needed. The physical properties of the rubber can be controlled by adjusting the proportions of the monomer units which form the acrylic rubber. In one embodiment of the present invention, the term "(meth)acrylic" indicates acrylic and/or methacrylic.

The acrylic rubber is known as a rubber having high oil resistance, particularly, high oil resistance under high temperature and having high heat resistance, and has been in increasing demand as hoses for automobiles, oil seals, O-rings, conveyor belts built in apparatuses and machines, and the like.

Any (meth)acrylic acid ester monomer can form the (meth)acrylic acid ester monomer unit as the main component of the acrylic rubber without limitation. Preferred examples thereof include alkyl (meth)acrylate monomers, alkoxyalkyl (meth)acrylate monomers, and the like.

Any alkyl (meth)acrylate monomers can be used without limitation. Preferred are esters of $C_1$ to $C_8$ alkanols and (meth)acrylic acid. Specifically, examples thereof include methyl (meth)acrylate, ethyl (meth)acrylate, n-propyl (meth)acrylate, n-butyl (meth)acrylate, isopropyl (meth)acrylate, isobutyl (meth)acrylate, n-hexyl (meth)acrylate, 2-ethylhexyl (meth)acrylate, cyclohexyl (meth)acrylate, and the like. Among these monomers, preferred are ethyl (meth)acrylate and n-butyl (meth)acrylate, and more preferred are ethyl acrylate and n-butyl acrylate. These may be used alone or in combination.

Any alkoxyalkyl (meth)acrylate monomer can be used without limitation. Preferred are esters of $C_2$ to $C_8$ alkoxyalkyl alcohols and (meth)acrylic acid. Specifically, examples thereof include methoxymethyl (meth)acrylate, ethoxymethyl (meth)acrylate, 2-methoxyethyl (meth)acrylate, 2-ethoxyethyl (meth)acrylate, 2-propoxyethyl (meth)acrylate, 2-butoxyethyl (meth)acrylate, 3-methoxypropyl (meth)acrylate, 4-methoxybutyl (meth)acrylate, and the like. Among these, preferred are 2-ethoxyethyl (meth)acrylate and 2-methoxyethyl (meth)acrylate, and particularly preferred are 2-ethoxyethyl acrylate and 2-methoxyethyl acrylate. These may be used alone or in combination.

The content of the (meth)acrylic acid ester monomer unit in the acrylic rubber is 50 to 100% by weight, preferably 60 to 99.5% by weight, more preferably 70 to 99.5% by weight. An excessively small content of the (meth)acrylic acid ester monomer unit may result in a cross-linked rubber having reduced weatherability, heat resistance, and oil resistance.

The (meth)acrylic acid ester monomer unit preferably comprises 30 to 100% by weight of the alkyl (meth)acrylate ester monomer unit and 70 to 0% by weight of the alkoxyalkyl (meth)acrylate ester monomer unit.

Any cross-linkable monomer which forms the cross-linkable monomer unit can be used without limitation. Examples thereof include α,β-ethylenically unsaturated carboxylic acid monomers; monomers having a halogen atom or an epoxy group; diene monomers; and the like.

Any α,β-ethylenically unsaturated carboxylic acid monomer can be used without limitation. Examples thereof include monoesters of $C_3$ to $C_{12}$ α,β-ethylenically unsaturated monocarboxylic acids, $C_4$ to $C_{12}$ α,β-ethylenically unsaturated dicarboxylic acids, and $C_4$ to $C_{12}$ α,β-ethylenically unsaturated dicarboxylic acids with $C_1$ to $C_8$ alkanols. Examples of $C_3$ to $C_{12}$ α,β-ethylenically unsaturated monocarboxylic acids include acrylic acid, methacrylic acid, α-ethylacrylic acid, crotonic acid, cinnamic acid, and the like. Examples of the $C_4$ to $C_{12}$ α,β-ethylenically unsaturated dicarboxylic acids include butenedioic acids such as fumaric acid and maleic acid, itaconic acid, citraconic acid, chloromaleic acid, and the like. Examples of the monoesters of $C_4$ to $C_{12}$ α,β-ethylenically unsaturated dicarboxylic acids with $C_1$ to $C_8$ alkanols include linear mono-alkyl esters of butenedioic acids, such as monomethyl fumarate, monoethyl fumarate, monobutyl fumarate, monomethyl maleate, monoethyl maleate, and monobutyl maleate; butenedioic acid monoesters having an alicyclic structure, such as monocyclopentyl fumarate, monocyclohexyl fumarate, monocyclohexenyl fumarate, monocyclopentyl maleate, monocyclohexyl maleate, and monocyclohexenyl maleate; itaconic acid monoesters such as monomethyl itaconate, monoethyl itaconate, monobutyl itaconate, and monocyclohexyl itaconate; and the like. Among these, preferred are linear mono-alkyl esters of butenedioic acids or butenedioic acid monoesters having an alicyclic structure, and more preferred are monobutyl fumarate, monobutyl maleate, monocyclohexyl fumarate, and monocyclohexyl maleate. These α,β-ethylenically unsaturated carboxylic acid monomers can be used alone or in combination. Among the monomers described above, the dicarboxylic acids may be copolymerized as anhydrides, which generate a carboxyl group as a result of hydrolysis during cross-linking.

Any monomer having a halogen atom can be used without limitation. Examples thereof include unsaturated alcohol esters of halogen-containing saturated carboxylic acids, haloalkyl (meth)acrylates, haloacyloxyalkyl (meth)acrylates, (haloacetylcarbamoyloxy)alkyl (meth)acrylates, halogen-containing unsaturated ethers, halogen-containing unsaturated ketones, halomethyl group-containing aromatic vinyl compounds, halogen-containing unsaturated amides, haloacetyl group-containing unsaturated monomers, and the like. Examples of the unsaturated alcohol esters of halogen-containing saturated carboxylic acids include vinyl chloroacetate, vinyl 2-chloropropionate, allyl chloroacetate, and the like. Examples of the haloalkyl (meth)acrylates include chloromethyl (meth)acrylate, 1-chloroethyl (meth)acrylate, 2-chloroethyl (meth)acrylate, 1,2-dichloroethyl (meth)acrylate, 2-chloropropyl (meth)acrylate, 3-chloropropyl (meth)acrylate, 2,3-dichloropropyl (meth)acrylate, and the like. Examples of the haloacyloxyalkyl (meth)acrylates include 2-(chloroacetoxy)ethyl (meth)acrylate, 2-(chloroacetoxy) propyl (meth)acrylate, 3-(chloroacetoxy) propyl (meth)acrylate, 3-(hydroxychloroacetoxy) propyl (meth)acrylate, and the like. Examples of the (haloacetylcarbamoyloxy)alkyl (meth)acrylates include 2-(chloroacetylcarbamoyloxy)ethyl (meth)acrylate, 3-(chloroacetylcarbamoyloxy)propyl (meth)acrylate, and the like. Examples of the halogen-containing unsaturated ethers include chloromethyl vinyl ether, 2-chloroethyl vinyl ether, 3-chloropropyl vinyl ether, 2-chloroethyl allyl ether, 3-chloropropyl allyl ether, and the like. Examples of the halogen-containing unsaturated ketones include 2-chloroethyl vinyl ketone, 3-chloropropyl vinyl ketone, 2-chloroethyl allyl ketone, and the like. Examples of the halomethyl group-containing aromatic vinyl compounds include p-chloromethylstyrene, p-chloromethyl-α-methylstyrene, and the like. Examples of the halogen-containing unsaturated amides include N-chloromethyl-(meth)acrylamide, and the like. Examples of the haloacetyl group-containing unsaturated monomers include 3-(hydroxychloroacetoxy)propyl allyl ether, p-vinylbenzyl chloroacetic acid esters, and the like.

Any monomer having an epoxy group can be used without limitation. Examples thereof include epoxy group-containing (meth)acrylates, epoxy group-containing ethers, and the like. Examples of the epoxy group-containing (meth) acrylates include glycidyl (meth)acrylate, and the like. Examples of the epoxy group-containing ethers include allyl glycidyl ether, and the like.

Examples of the diene monomers include conjugated diene monomers and non-conjugated diene monomers. Examples of the conjugated diene monomers include 1,3-butadiene, isoprene, piperylene, and the like. Examples of the non-conjugated diene monomers include ethylidene norbornene, dicyclopentadiene, dicyclopentadienyl (meth)acrylate, 2-dicyclopentadienylethyl (meth)acrylate, and the like.

These cross-linkable monomers can be used alone or in combination. The content of the cross-linkable monomer unit in the acrylic rubber is 0 to 10% by weight, preferably 0.5 to 7% by weight, more preferably 0.5 to 5% by weight. An excessively large content of the cross-linkable monomer unit may result in a cross-linked rubber having a reduced elongation or an increased compression set.

Any other monomer copolymerizable with the monomers described above can be used without limitation. Examples thereof include aromatic vinyl monomers, α,β-ethylenically unsaturated nitrile monomers, monomers having two or more acryloyloxy groups, olefin monomers, vinyl ether compounds, and the like.

Examples of the aromatic vinyl monomers include styrene, α-methylstyrene, divinylbenzene, and the like. Examples of the α,β-ethylenically unsaturated nitrile monomers include acrylonitrile, methacrylonitrile, and the like. Examples of polyfunctional (meth)acrylic monomers include (meth)acrylic acid diesters of ethylene glycol, (meth)acrylic acid diesters of propylene glycol, and the like. Examples of the olefin monomers include ethylene, propylene, 1-butene, 1-octene, and the like. Examples of the vinyl ether compounds include vinyl acetate, ethyl vinyl ether, butyl vinyl ether, and the like. Among these, preferred are styrene, acrylonitrile, and methacrylonitrile, and more preferred are acrylonitrile and methacrylonitrile.

These other copolymerizable monomers can be used alone or in combination. The content of the unit of the other monomer in the acrylic rubber is 0 to 50% by weight, preferably 0 to 39.5% by weight, more preferably 0 to 29.5% by weight.

The acrylic rubber used in one embodiment of the present invention can be prepared through polymerization of the monomers described above. The polymerization reaction can be performed by any one of emulsion polymerization, suspension polymerization method, bulk polymerization, and solution polymerization. Preferred is emulsion polymerization under ambient pressure, which is usually used as a known method of producing acrylic rubber, because the polymerization reaction is easily controlled.

Emulsion polymerization may be performed by any of a batchwise method, a semi-batchwise method, and a continuous method. The polymerization is performed usually in the temperature range of 0 to 70° C., preferably 5 to 50° C.

The acrylic rubber used in one embodiment of the present invention thus produced has a Mooney viscosity [ML1+4, 100° C.] (polymer Mooney) of preferably 10 to 80, more preferably 20 to 70, particularly preferably 25 to 60.

<Other Additives, Process of Preparing Polymer Composition, and the Like>

The polymer composition according to one embodiment of the present invention may further contain other additives in addition to the polymer and, as an antioxidant, the diarylamine-based compound represented by General Formula (1) or the composition comprising the diarylamine-based compound represented by General Formula (1) and the condensed heterocyclic compound represented by General Formula (19).

Examples of the other additives include additives usually used in the fields using synthetic polymer materials. Examples thereof include reinforcing fillers such as carbon black and silica; non-reinforcing fillers such as calcium carbonate and clay; light stabilizers; scorching preventing agents; plasticizers; processing aids; greases; tackifiers; lubricant; flame retardants; antifungal agents; antistatic agents; colorants; silane coupling agents; cross-linking agents; cross-linking accelerators; cross-linking retarders; and the like.

These additives can be used in any compounding amounts in the range not impairing the object and effects of one embodiment of the present invention, and can be appropriately compounded in the amounts according to the purposes of compounding.

The polymer composition according to one embodiment of the present invention can be prepared, for example, by mixing and kneading the ingredients with a Banbury mixer, a kneader, or the like, and then further kneading the ingredients with a kneading roll. Although the ingredients can be compounded in any order, in a preferred order, ingredients which barely react or decompose by heat are sufficiently mixed, and then those which readily react or decompose by heat, such as a cross-linking agent, are mixed in a short time at a temperature at which the reaction and the decomposition thereof are avoided.

For example, in the case where a rubber such as an acrylic rubber is used as a polymer constituting the polymer composition and the cross-linking agent is contained, a cross-linked rubber can be prepared through cross-linking of the composition. The cross-linked rubber can be prepared by forming with a forming machine having a desired shape, such as an extruder, an injection molding machine, a compressor, a roll, or the like, and solidifying the cross-linked rubber into a desired shape through a cross-linking reaction. In this operation, the ingredients may be cross-linked after preliminary forming, or may be formed and cross-linked at the same time. The forming temperature is usually 10 to 200° C., preferably 25 to 120° C. The cross-linking temperature is usually 130 to 220° C., preferably 150 to 190° C. The cross-linking time is usually 2 minutes to 10 hours, preferably 3 minutes to 6 hours. The heating method may be appropriately selected from methods used to cross-link rubber, such as press heating, steam heating, oven heating, and hot air heating.

The cross-linked rubber, although cross-linked on its surface, may be insufficiently cross-linked in its inside depending on the shape, the size, and the like. Thus, the cross-linked rubber may be secondarily cross-linked by further heating. The time for secondary cross-linking is preferably 1 to 48 hours although it varies according to the heating method, the cross-linking temperature, the shape, and the like. The heating method and the heating temperature may be appropriately selected.

The cross-linked rubber thus obtained has high heat resistance. For this reason, utilizing the properties, the cross-linked rubber prepared with the rubber composition above is suitably used as a variety of seals such as O-rings, packings, diaphragms, oil seals, shaft seals, bearing seals, mechanical seals, wellhead seals, seals for electrical and electronic devices, and seals for pneumatic apparatuses and devices; a variety of gaskets such as a cylinder head gasket attached to a connection between a cylinder block and a cylinder head, a rocker cover gasket attached to a connection between a rocker cover and a cylinder head, an oil pan gasket attached to a connection between an oil pan and a cylinder block or a transmission case, a gasket for fuel cell separators attached between a pair of housings which sandwich a unit cell including a positive electrode, an electrolyte plate, and a negative electrode, and a gasket for top covers for hard disk drives; a variety of belts; a variety of hoses such as fuel hoses, turbo air hoses, oil hoses, radiator hoses, heater hoses, water hoses, vacuum brake hoses, control hoses, air conditioner hoses, brake hoses, power steering hoses, air hoses, marine hoses, risers, and flow lines; a variety of boots such as CVJ boots, propeller shaft boots, constant-velocity joint boots, and rack and pinion boots; and rubber parts for damping materials such as cushion materials, dynamic dampers, rubber couplings, air springs, and vibration insulators. In particular, the cross-linked rubber can also be suitable used in applications under severe and high temperatures.

EXAMPLES

One embodiment of the present invention will now be described more specifically by way of Examples and Comparative Examples. In each example, the term "parts" is weight-based unless otherwise specified.

The physical properties were evaluated according to the following methods.

[Measurement of Pyrolysis Temperature of Antioxidant]

The pyrolysis temperature of an antioxidant was measured using a simultaneous thermogravimetry and differential thermal analyzer ("TG/DTA7200", made by SII). Specifically, the antioxidant was heated according to the following heating program, and the temperature at which the reduction in weight exceeded 10 μg/min was defined as a pyrolysis temperature.

Heating program: Heating from 30° C. at 5° C./min→Holding at 50° C. for 30 minutes→Heating at 10° C./min→Holding at 400° C. for 5 minutes

[Measurement of Peak Top Molecular Weight (Mp) of Acrylic Polymer]

The peak top molecular weight (Mp) of the acrylic polymer was determined as a molecular weight in terms of polystyrene by dissolving a film of polymer composition in DMF, and measuring the solution by gel permeation chromatography (GPC). The specific condition for measurement is shown below. In this measurement, it was determined that molecular weights of 1000 or less were derived from the antioxidant, and such molecular weights were not considered in the determination of the peak top molecular weight (Mp) of the acrylic polymer.

Apparatus: high-performance liquid chromatograph HPC-8220 GPC made by Tosoh Corporation Columns: two SupeR AWM-H columns (in series) made by Tosoh Corporation Temperature: 40° C.

Detector: RI-8220 made by Tosoh Corporation

Eluent: DMF (containing 10 mmol/L lithium bromide)

[Suppression of Reduction in Molecular Weight]

A film of polymer composition was heated in air at 190° C. for 144 hours to yield the film of polymer composition after heating. The peak top molecular weight (Mp) of the acrylic polymer contained in the film of polymer composition after heating was determined in the same manner as described above, and the suppression (%) of reduction in molecular weight was calculated from the following expression. It can be determined that a higher suppression of reduction in molecular weight indicates higher resistance against thermal degradation and a higher antioxidant effect.

Suppression(%) of reduction in molecular weight=
("peak top molecular weight of acrylic polymer after heating"/"peak top molecular weight of acrylic polymer before heating")×100

[Measurement of Proportion of Residual Antioxidant in System after Heating]

The proportion of residual antioxidant in the system after heating was measured as follows.

First, as in Section [Measurement of peak top molecular weight (Mp) of acrylic polymer] described above, a film of polymer composition was dissolved in DMF, and the solution was measured by liquid chromatography (LC) to determine the amount of antioxidant in the polymer composition before heating. The specific condition for measurement is shown below.

Apparatus: Agilent 1200 series
Column: Agilent ZORBAX Bonus-RP, 4.6×250 nm, 5 μm or Agilent
ZORBAX Eclipse XDB-C18, 4.6×250 nm, 5 μm
Temperature: 40° C.
Detector: UV (254.4 nm or 270.4 nm)
Eluent: acetonitrile (1 mL/min)

In the next step, the film of polymer composition after heating was prepared by the same method as that in Section [Suppression of reduction in molecular weight] above. The film of polymer composition after heating was dissolved in DMF, and the solution was measured by liquid chromatography in the same manner as above to determine the amount of antioxidant in the polymer composition after heating. Using the results of measurement, the proportion (%) of residual antioxidant after heating in the system was calculated from the following expression:

Proportion(%) of residual antioxidant in system after heating=("amount of antioxidant in polymer composition after heating"/"amount of antioxidant in polymer composition before heating")×100

Synthetic Example 1: Synthesis of Compound 1

15.00 g of 4,4'-diaminodiphenylamine sulfate hydrate, 16.46 g of phthalic anhydride, 140 cc of acetic acid, and 70 cc of N-methylpyrrolidinone were placed into a 500-cc four-necked flask provided with a reflux cooler, and were heated at 125° C. for 2.5 hours. After the heating was completed, the reaction solution was cooled to room temperature, 140 cc of methanol was added, and the precipitate was filtered. The precipitate was washed with 120 cc of methanol, was suspended in 140 cc of N-methylpyrrolidinone, and was dissolved by heating to 100° C. After cooling the solution to room temperature, 280 cc of methanol was added, and the precipitate was filtered. The precipitate was washed with 130 cc of methanol, and was dried under reduced pressure to yield 18.53 g of Compound 1 represented by General Formula (11) above where $R^{11}$, $R^{12}$, $R^{13}$, $R^{14}$, $R^{15}$, $R^{16}$, $R^{17}$, and $R^{18}$ all are a hydrogen atom, and $A^1$ and $A^2$ all are a 1,4-phenylene group, molecular weight: 459.45) with a yield of 80%. The structure was identified by $^1$H-NMR. $^1$H-NMR (500 MHz, DMSO-d6, TMS, δ ppm): δ 7.25 (dd, J=2.0, 6.5 Hz, 4H), 7.31 (dd, J=2.0, 6.5 Hz, 4H), 7.90 (dd, J=3.0, 5.5 Hz, 4H), 7.96 (dd, J=3.0, 5.5 Hz, 4H), 8.65 (s, 1H). The pyrolysis temperature measured by the method above was 362° C.

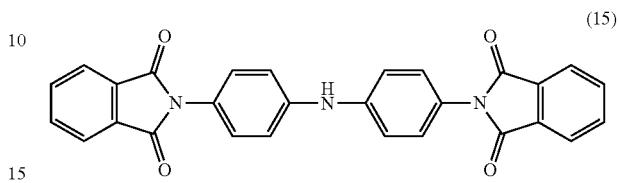

(15)

Synthetic Example 2: Synthesis of Compound 2

5.00 g of 4,4'-diaminodiphenylamine sulfate hydrate, 7.97 g of 2,3-naphthalenedicarboxylic anhydride, 40 cc of acetic acid, and 60 cc of N-methylpyrrolidinone were placed into a 200-cc four-necked flask provided with a reflux cooler, and were heated at 130° C. for 1.7 hours. After the heating was completed, the reaction solution was cooled to roam temperature, and the precipitate was filtered. The precipitate was washed with 100 cc of methanol, and was suspended with 120 cc of N-methylpyrrolidinone. The suspension was heated to 120° C., and was cooled to room temperature, followed by filtration. The residue was washed with 100 cc of methanol, and then with 200 cc of THF, and was dried at 180° C. under reduced pressure to yield 7.36 g of Compound 2 represented by General Formula (18) below (compound represented by General Formula (13) above where $R^{11}$, $R^{12}$, $R^{13}$, $R^{14}$, $R^{15}$, $R^{16}$, $R^{17}$, $R^{18}$, $R^{19}$, $R^{20}$, $R^{21}$, and $R^{22}$ all are a hydrogen atom, and $A^1$ and $A^2$ all are a 1,4-phenylene group, molecular weight: 559.57) with a yield of 78%. The structure was identified by $^1$H-NMR. $^1$H-NMR (500 MHz, DMSO-d6, TMS, δ ppm): δ 7.28 (d, J=9.0 Hz, 4H), 7.38 (d, J=9.0 Hz, 4H), 7.81 (dd, J=3.0, 6.0 Hz, 4H), 8.32 (dd, J=3.0, 6.0 Hz, 4H), 8.62 (s, 4H), 8.69 (s, 1H). The pyrolysis temperature measured by the method above was 400° C. or more.

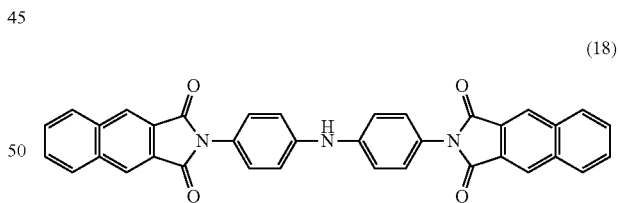

(18)

Synthetic Example 3: Synthesis of Compound 3

5.02 g of 4,4'-diaminodiphenylamine sulfate hydrate, 6.66 g of hexahydro-4,7-methanoisobenzofuran-1,3-dione, 40 cc of acetic acid, and 20 cc of N-methylpyrrolidinone were placed into a 200-cc four-necked flask provided with a reflux cooler, and were heated at 125° C. for 2 hours. After the heating was completed, the reaction solution was cooled to room temperature, 60 cc of methanol was added, and the precipitate was filtered. The precipitate was washed with 100 cc of methanol, was suspended in 40 cc of N-methylpyrrolidinone, and was dissolved by heating to 120° C. After cooling the solution to room temperature, 60 cc of methanol was added, and the precipitate was filtered. The precipitate was washed with 140 cc of methanol, and was dried under reduced pressure to yield 6.20 g of Compound 3 represented by General Formula (17) below (compound represented by General Formula (12) above where $R^{11}$, $R^{12}$, $R^{13}$, $R^{14}$, $R^{15}$, $R^{16}$, $R^{17}$, and $R^{18}$ all are a hydrogen atom, and $A^1$ and $A^2$ all are a 1,4-phenylene group, molecular weight: 495.57) with a yield of 75%. The structure was identified by $^1$H-NMR. $^1$H-NMR (500 MHz, DMSO-d6, TMS, δ ppm): δ 1.27 (dd, J=1.5, 8.5 Hz, 4H), 1.55 (d, J=10.0 Hz, 4H), 1.58 (d, J=10.0 Hz, 2H), 1.67 (d, J=10.0 Hz, 2H), 2.67 (s, 4H), 3.24 (s, 4H), 7.07 (d, J=8.5 Hz, 4H), 7.18 (d, J=8.5 Hz, 4H), 8.60 (s, 1H). The pyrolysis temperature measured by the method above was 368° C.

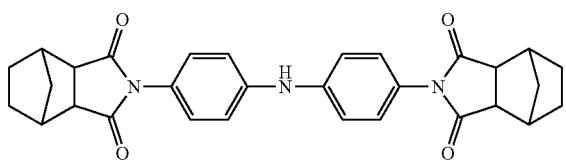

(17)

Synthetic Example 4: Synthesis of Compound 4

5.00 g of 4,4'-diaminodiphenylamine sulfate hydrate, 4.05 g of succinic anhydride, 40 cc of acetic acid, and 20 cc of N-methylpyrrolidinone were placed into a 200-cc four-necked flask provided with a reflux cooler, and was heated at 125° C. for 1.6 hours. After the heating was completed, the reaction solution was cooled to room temperature. 180 cc of methanol was added, and the precipitate was filtered. The precipitate was washed with 20 cc of methanol, and was suspended in 30 cc of N-methylpyrrolidinone. The precipitate was dissolved by heating to 70° C. After cooling the solution to room temperature, 120 cc of methanol was added, and the precipitate was filtered, was washed with 170 cc of methanol, and was dried under reduced pressure to yield 2.84 g of Compound 4 represented by General Formula (14) (compound represented by General Formula (10) above where $R^{11}$, $R^{12}$, $R^{13}$, and $R^{14}$ all are a hydrogen atom, and $A^1$ and $A^2$ all are a 1,4-phenylene group, molecular weight: 363.37) with a yield of 46%. The structure was identified by $^1$H-NMR. $^1$H-NMR (500 MHz, DMSO-d6, TMS, δ ppm): δ 2.76 (s, 8H), 7.11 (dd, J=2.0, 7.0 Hz, 4H), 7.17 (dd, J=2.0, 7.0 Hz, 4H), 8.55 (s, 1H). The pyrolysis temperature measured by the method above was 339° C.

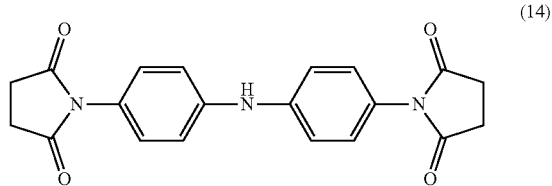

(14)

Synthetic Example 5: Synthesis of Compound 5

5.01 g of 4,4'-diaminodiphenylamine sulfate hydrate, 6.66 g of 4-methylphthalic anhydride, 40 cc of acetic acid, and 20 cc of N-methylpyrrolidinone were placed into a 200-cc four-necked flask provided with a reflux cooler, and were heated at 125° C. for 1.7 hours. After the heating was completed, the reaction solution was cooled to room temperature. 60 cc of methanol was added, and the precipitate was filtered. The precipitate was washed with 100 cc of methanol, and was suspended in 50 cc of N-methylpyrrolidinone. The suspension was heated to 120° C., and was cooled to room temperature. 100 cc of methanol was added, and the precipitate was filtered. The precipitate was washed with 100 cc of methanol, and was dried at 180° C. under reduced pressure to yield 6.70 g of Compound 5 represented by General Formula (16) (compound represented by General Formula (11) where $R^{11}$, $R^{13}$, $R^{14}$, $R^{15}$, $R^{17}$, and $R^{18}$ all are a hydrogen atom, $R^{12}$ and $R^{16}$ all are a methyl group, and $A^1$ and $A^2$ all are a 1,4-phenylene group, molecular weight: 487.51) with a yield of 82%. The structure was identified by $^1$H-NMR. $^1$H-NMR (500 MHz, DMSO-d6, TMS, δ ppm): δ 2.50 (t, J=1.5 Hz, 6H), 7.24 (d, J=8.5 Hz, 4H), 7.30 (d, J=8.5 Hz, 4H), 7.70 (d, J=7.5 Hz, 2H), 7.79 (s, 2H), 7.84 (d, J=7.5 Hz, 2H), 8.64 (s, 1H). The pyrolysis temperature measured by the method above was 379° C.

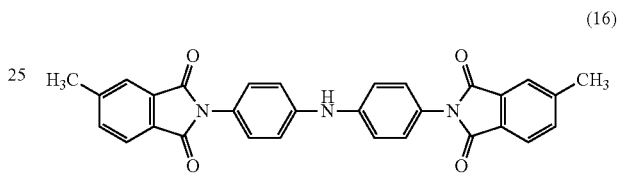

(16)

Synthetic Example 6: Synthesis of Compound 6

50.0 g of phenothiazine was placed into a three-necked reactor provided with a thermometer in a nitrogen stream, and was dissolved in 200 ml of toluene. In the next step, 59.31 g of α-methylstyrene and 1.19 g of p-toluenesulfonic acid monohydrate were added to this solution to perform a reaction at 80° C. for one hour. The reaction solution was then cooled to room temperature. 48 ml of acetic acid and 85.34 g of a 30% hydrogen peroxide solution were added to further perform a reaction at 80° C. for 2 hours. The reaction solution was cooled to roam temperature, 630 ml of methanol was added, and the precipitated crystals were filtered. The crystals were rinsed with 320 ml of methanol to yield 85.7 g of Compound 6 represented by General Formula (20) with a yield of 73%. The structure was identified by $^1$H-NMR. $^1$H-NMR (500 MHz, DMSO-d6, TMS, δ ppm): 1.67 (s, 12H), 7.15-7.32 (m, 12H), 7.43 (dd, 2H, J=9.0, 2.0 Hz), 7.68 (d, 2H, J=1.5 Hz), 10.84 (s, 1H). The pyrolysis temperature measured by the method above was 341° C.

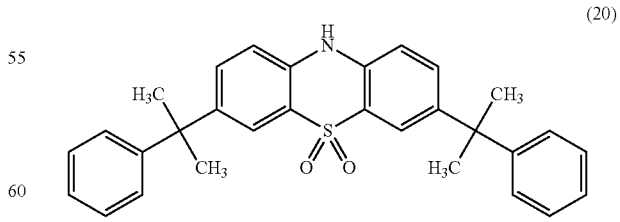

(20)

Synthetic Example 7: Synthesis of Compound 7

80 g of trimellitic anhydride and 76.7 g of 4-aminodiphenylamine were dissolved in 1 liter of acetic acid in a nitrogen stream in a four-necked reactor provided with a cooler and a thermometer. This solution was reacted in an oil bath by heating under reflux for 10 hours. After the reaction was completed, the reaction solution was added to 2 liter of water to precipitate a solid. Subsequently, the precipitated solid was vacuum filtered. The residue was washed with water and methanol in this order, and was dried in a vacuum dryer to yield 138.5 g of an intermediate product represented by General Formula (34) below with a yield of 92%. The structure was identified by $^1$H-NMR. $^1$H-NMR (500 MHz, THF-d8, TMS, δ ppm): 6.97 (t, 1H, J=7.0 Hz), 7.24-7.28 (m, 4H), 7.33-7.36 (m, 2H), 7.40-7.42 (m, 2H), 7.68 (s, 1H), 8.11 (d, 1H, J=8.5 Hz), 8.56-8.58 (m, 2H) 12.20 (bs 1H).

(34)

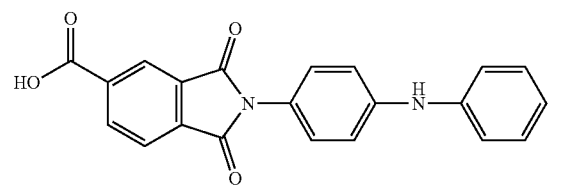

In the next step, 10 g of the intermediate product represented by General Formula (34) above, 4.8 g of 2-naphthol, and 400 mg of N,N-dimethyl-4-aminopyridine were dissolved in 150 ml of N-methylpyrrolidone in a nitrogen stream in a four-necked reactor provided with a cooler, a thermometer, and a dropping funnel. 6.4 g of 1-ethyl-3-(3-dimethylaminopropyl) carbodiimide hydrochloride (WSC) was added to this solution under room temperature, and then was reacted under room temperature for 12 hours. After the reaction was completed, the reaction solution was added to methanol to precipitate a solid. The precipitated solid was vacuum filtered. The resulting solid was refined by silica gel column chromatography (toluene:ethyl acetate=9:1) to yield 7.4 g of Compound 7 represented by General Formula (35) with a yield of 55%. The structure was identified by $^1$H-NMR. $^1$H-NMR (500 MHz, DMF-d7, TNS, δ ppm): 6.93 (t, 1H, J=7.0 Hz), 7.24-7.33 (m, 6H), 7.43 (d, 2H, J=8.5 Hz), 7.58-7.66 (m, 3H), 8.01-8.07 (m, 3H), 8.13 (d, 1H, J=9.0 Hz), 8.24 (d, 1H, J=8.0 Hz), 8.49 (s, 1H), 8.62 (d, 1H, J=1.0 Hz), 8.74 (dd, 1H, J=1.5 Hz, 8.0 Hz). The pyrolysis temperature measured by the method above was 326° C.

(35)

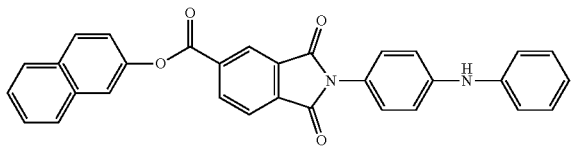

Synthetic Example 8: Synthesis of Compound 8

30.0 g of phenothiazine was placed into a three-necked reactor provided with a thermometer in a nitrogen stream, and was dissolved in 175 ml of toluene. In the next step, 35.58 g of α-methylstyrene and 0.72 g of p-toluenesulfonic acid monohydrate were added to this solution to perform a reaction at 80° C. for one hour. After cooling the reaction solution to roam temperature, 60 ml of acetic acid was added, and 17.07 g of a 30% hydrogen peroxide solution was slowly added dropwise over 30 minutes to further perform a reaction at room temperature for 2 hours. Subsequently, 760 ml of methanol was added to the reaction solution, and the precipitated crystals were filtered. The crystals were rinsed with 380 ml of methanol to yield 55.5 g of Compound 8 represented by General Formula (21) with a yield of 82%. The structure was identified by $^1$H-NMR. $^1$H-NMR (500 MHz, DMSO-d6, TMS, δ ppm): δ 1.68 (s, 6H), 1.70 (s, 6H), 7.15-7.32 (m, 12H), 7.38 (dd, 2H, J=9.0, 2.0 Hz), 7.70 (d, 2H, J=1.5 Hz), 10.85 (s, 1H). The pyrolysis temperature measured by the method above was 260° C.

(21)

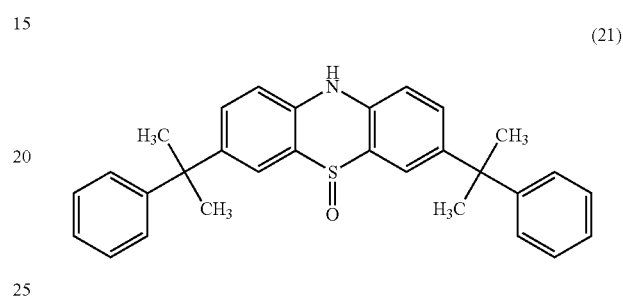

Synthetic Example 9: Synthesis of Acrylic Polymer (Poly(Ethyl Acrylate))

200 parts of water, 3 parts of sodium lauryl sulfate, and 100 parts of ethyl acrylate were placed into a polymerization reactor provided with a thermometer, a stirrer, a nitrogen inlet pipe, and a depressurizer. Oxygen was sufficiently removed through degassing under reduced pressure and purging with nitrogen, and 0.002 parts of sodium formaldehyde sulfoxylate and 0.005 parts of cumene hydroperoxide were added to initiate an emulsion polymerization reaction under ambient pressure and ambient temperature. The reaction was continued until the polymerization conversion rate reached 95%. A polymerization terminator was added to terminate polymerization. The resulting polymer emulsion was coagulated with an aqueous solution of magnesium sulfate, followed by washing with water and drying. A rubbery acrylic polymer (poly(ethyl acrylate)) was thereby yielded.

Example 1

1 g of the acrylic polymer (poly(ethyl acrylate)) yielded in Synthetic Example 9 was dissolved in 9 g of THF to prepare a solution, and 22.7 mg of Compound 1 yielded in Synthetic Example 1 was added as an antioxidant to this solution, followed by stirring overnight. A 1.2-g portion of the mixture was placed into a 6-cc sample bottle, and was dried at 40° C. under reduced pressure overnight to prepare a film of polymer composition. Using the resulting film of polymer composition, the peak top molecular weight (Mp) of the acrylic polymer before heating and the peak top molecular weight (Mp) of the acrylic polymer after heating at 190° C. for 144 hours were measured by the method described above. The peak top molecular weight of the acrylic polymer before heating was 738,072, and that after heating for 144 hours was 370,455. The suppression of reduction in molecular weight was 50.2%. The proportion of residual antioxidant in the system after heating at 190° C. for 144 hours was measured by the method described above. The proportion of residual antioxidant in the system was 100.0%.

Example 2

A film of polymer composition was prepared in the same manner as in Example 1 except that as the antioxidant, Compound 1 was replaced with 27.6 mg of Compound 2 yielded in Synthetic Example 2. Evaluation was performed in the same manner as in Example 1. The peak top molecular weight of the acrylic polymer before heating was 816,697, and that after heating for 144 hours was 280,145. The suppression of reduction in molecular weight was 34.3%. The proportion of residual antioxidant in the system was 99.8%.

Example 3

A film of polymer composition was prepared in the same manner as in Example 1 except that as the antioxidant, Compound 1 was replaced with 24.4 mg of Compound 3 yielded in Synthetic Example 3. Evaluation was performed in the same manner as in Example 1. The peak top molecular weight of the acrylic polymer before heating was 826,040, and that after heating for 144 hours was 250,217. The suppression of reduction in molecular weight was 30.3%. The proportion of residual antioxidant in the system was 74.3%.

Example 4

A film of polymer composition was prepared in the same manner as in Example 1 except that as the antioxidant, Compound 1 was replaced with 17.9 mg of Compound 4 yielded in Synthetic Example 4. Evaluation was performed in the same manner as in Example 1. The peak top molecular weight of the acrylic polymer before heating was 798,286, and that after heating for 144 hours was 259,836. The suppression of reduction in molecular weight was 32.5%. The proportion of residual antioxidant in the system was 100.0%.

Example 5

A film of polymer composition was prepared in the same manner as in Example 1 except that as the antioxidant, Compound 1 was replaced with 24.0 mg of Compound 5 yielded in Synthetic Example 5. Evaluation was performed in the same manner as in Example 1. The peak top molecular weight of the acrylic polymer before heating was 780,238, and that after heating for 144 hours was 298,213. The suppression of reduction in molecular weight was 38.2%. The proportion of residual antioxidant in the system was 95.7%.

Comparative Example 1

A film of polymer composition was prepared in the same manner as in Example 1 except that as the antioxidant, Compound 1 was replaced with 23.1 mg of Compound 6 yielded in Synthetic Example 6. Evaluation was performed in the same manner as in Example 1. The peak top molecular weight of the acrylic polymer before heating was 798,286, and that after heating for 144 hours was 125,945. The suppression of reduction in molecular weight was 15.8%. The proportion of residual antioxidant in the system was 88.0%.

Comparative Example 2

A film of polymer composition was prepared in the same manner as in Example 1 except that as the antioxidant, Compound 1 was replaced with 23.9 mg of Compound 7 yielded in Synthetic Example 7. Evaluation was performed in the same manner as in Example 1. The peak top molecular weight of the acrylic polymer before heating was 746,832, and that after heating for 144 hours was 202,235. The suppression of reduction in molecular weight was 27.1%. The proportion of residual antioxidant in the system was 44.0%.

Comparative Example 3

A film of polymer composition was prepared in the same manner as in Example 1 except that as the antioxidant, Compound 1 was replaced with 20.0 mg of Compound 9 (4,4'-bis($\alpha,\alpha$-dimethylbenzyl)diphenylamine, trade name "NOCRAC CD", made by Ouchi Shinko Chemical Industrial Co., Ltd., pyrolysis temperature: 252° C.). Evaluation was performed in the same manner as in Example 1. The peak top molecular weight of the acrylic polymer before heating was 746,832, and that after heating for 144 hours was 107,527. The suppression of reduction in molecular weight was 14.4%. The proportion of residual antioxidant in the system was 9.7%.

TABLE 1

| | Compound | Molecular weight | Thermal decomposition temperature (° C.) | Amount added relative to 1 g of acrylic polymer (mg) | Amount compounded relative to 1 g of acrylic polymer (mmol) | Change after heating at 190° C. for 144 hours | |
|---|---|---|---|---|---|---|---|
| | | | | | | Suppression of reduction in molecular weight (%) | Proportion of residual antioxidant in system (%) |
| Example 1 | Compound 1 | 459.45 | 362 | 22.7 | 0.0494 | 50.2 | 100.0 |
| Example 2 | Compound 2 | 559.57 | >400 | 27.6 | 0.0493 | 34.3 | 99.8 |
| Example 3 | Compound 3 | 495.57 | 368 | 24.4 | 0.0492 | 30.3 | 74.3 |
| Example 4 | Compound 4 | 363.37 | 339 | 17.9 | 0.0493 | 32.5 | 100.0 |
| Example 5 | Compound 5 | 487.51 | 379 | 24.0 | 0.0492 | 38.2 | 95.7 |
| Comparative Example 1 | Compound 6 | 467.62 | 341 | 23.1 | 0.0494 | 15.8 | 88.0 |
| Comparative Example 2 | Compound 7 | 484.50 | 326 | 23.9 | 0.0493 | 27.1 | 44.0 |
| Comparative Example 3 | Compound 9 | 405.57 | 252 | 20.0 | 0.0493 | 14.4 | 9.7 |

Evaluation of Examples 1 to 5 and Comparative Examples 1 to 3

Table 1 shows that the polymer compositions according to Examples 1 to 5 where the diarylamine-based compound represented by General Formula (1) was used as the antioxidant favorably prevented a reduction in molecular weight of the polymer after heating at 190° C. for 144 hours. It also shows that the polymer compositions according to Examples 1 to 5 comprising the diarylamine-based compound represented by General Formula (1) had a high proportion of residual diarylamine-based compound represented by General Formula (1) in the system after heating at 190° C. for 144 hours, and also had a long-lasting antioxidant effect.

In contrast, among the polymer compositions according to Comparative Examples 1 to 3 comprising an antioxidant other than the diarylamine-based compound represented by General Formula (1), the polymer compositions according to Comparative Examples 1 and 3 exhibited a significant reduction in molecular weight of the polymer after heating at 190° C. for 144 hours. Furthermore, the polymer compositions according to Comparative Examples 2 and 3 exhibited a low proportion of residual antioxidant in the system, and thus its long-lasting antioxidant effect cannot be not expected.

Example 6

100 parts of acrylic rubber (trade name "Nipol AR212HR", made by ZECN Corporation), 50 parts of silica (trade name "Nipsil ER", made by TOSOH SILICA CORPORATION), 1 part of a silane coupling agent (trade name "KEM-403", made by Shin-Etsu Silicone), 2 parts of stearic acid, 1 part of ester wax (trade name "Gregg G8205", made by DIC Corporation), 5 parts of a plasticizer (trade name "ADEKA CIZER RS735", made by Adeka Corporation), and 1 part of Compound 1, as an antioxidant, which was yielded in Synthetic Example 1 were kneaded at 50° C. using a Banbury mixer. 0.5 parts of hexamethylenediamine carbamate (trade name "Diak No. 1", made by DuPont Dow Elastomers L.L.C.) as a cross-linking agent and 2 parts of di-o-tolylguanidine (trade name "NOCCELER DT", made by Ouchi Shinko Chemical Industrial Co., Ltd.) as a cross-linking accelerator were added, and the ingredients were kneaded at 50° C. with an open roll mill to prepare a polymer composition.

The resulting polymer composition was formed by pressing at 170° C. for 20 minutes, cross-linked, and further heated at 170° C. for 4 hours to yield a sheet-shaped cross-linked rubber. In the next step, a #3 dumbbell-shaped test piece was prepared from the cross-linked rubber, and was measured for elongations at break before and after heating according to JIS K6251. The heating was performed at 190° C. for 504 hours. The change in elongation at break before and after heating was determined from the following expression. The elongation at break before heating and the change in elongation before and after heating are shown in Table 2.

Change(%) in elongation before and after heating={("elongation (%) of test piece before heating"−"elongation(%) of test piece after heating")/"elongation(%) of test piece before heating"}×100

Example 7

A polymer composition and a cross-linked rubber were prepared in the same manner as in Example 6 except that the compounding amount of Compound 1 as the antioxidant was changed from 1 part to 2 parts, and were evaluated in the same manner as above. The results are shown in Table 2.

Example 8

A polymer composition and a cross-linked rubber were prepared in the same manner as in Example 7 except that 1 part of Compound 6 yielded in Synthetic Example 6 was further compounded as an antioxidant, and were evaluated in the same manner as above. The results are shown in Table 2.

Example 9

A polymer composition and a cross-linked rubber were prepared in the same manner as in Example 7 except that 0.5 parts of Compound 6 yielded in Synthetic Example 6 was further compounded as an antioxidant, and were evaluated in the same manner as above. The results are shown in Table 2.

Example 10

A polymer composition and a cross-linked rubber were prepared in the same manner as in Example 7 except that 1 part of Compound 8 yielded in Synthetic Example 8 was further compounded as an antioxidant, and were evaluated in the same manner as above. The results are shown in Table 2.

Comparative Example 4

A polymer composition and a cross-linked rubber were prepared in the same manner as in Example 6 except that as the antioxidant, Compound 1 was replaced with 1 part of Compound 6 yielded in Synthetic Example 6, and were evaluated in the same manner as above. The results are shown in Table 2.

Comparative Example 5

A polymer composition and a cross-linked rubber were prepared in the same manner as in Example 6 except that as the antioxidant, Compound 1 was replaced with 1 part of Compound 9, and were evaluated in the same manner as above. The results are shown in Table 2.

TABLE 2

|  |  | Example 6 | Example 7 | Example 8 | Example 9 | Example 10 | Comparative Example 4 | Comparative Example 5 |
|---|---|---|---|---|---|---|---|---|
| Formulation | | | | | | | | |
| Acrylic rubber | (parts) | 100 | 100 | 100 | 100 | 100 | 100 | 100 |
| Silica | (parts) | 50 | 50 | 50 | 50 | 50 | 50 | 50 |

TABLE 2-continued

|  |  | Example 6 | Example 7 | Example 8 | Example 9 | Example 10 | Comparative Example 4 | Comparative Example 5 |
|---|---|---|---|---|---|---|---|---|
| Silane coupling agent | (parts) | 1 | 1 | 1 | 1 | 1 | 1 | 1 |
| Stearic acid | (parts) | 2 | 2 | 2 | 2 | 2 | 2 | 2 |
| Ester wax | (parts) | 1 | 1 | 1 | 1 | 1 | 1 | 1 |
| Plasticizer | (parts) | 5 | 5 | 5 | 5 | 5 | 5 | 5 |
| Compound 1 | (parts) | 1 | 2 | 2 | 2 | 2 |  |  |
| Compound 6 | (parts) |  |  | 1 | 0.5 |  | 1 |  |
| Compound 8 | (parts) |  |  |  |  | 1 |  |  |
| Compound 9 | (parts) |  |  |  |  |  |  | 1 |
| Hexamethylenediamine carbamate | (parts) | 0.5 | 0.5 | 0.5 | 0.5 | 0.5 | 0.5 | 0.5 |
| Di-o-tolylguanidine | (parts) | 2 | 2 | 2 | 2 | 2 | 2 | 2 |
| Evaluation |  |  |  |  |  |  |  |  |
| Elongation at break before heating | (MPa) | 289 | 281 | 294 | 290 | 291 | 285 | 288 |
| Change in elongation before and after heating | (%) | 44 | 41 | 31 | 36 | 35 | 64 | 82 |

Evaluation of Examples 6 to 10 and Comparative Examples 4 and 5

Table 2 shows that the use of the polymer compositions of Examples 6 to 10 where the diarylamine-based compound represented by General Formula (1) was used as the antioxidant resulted in cross-linked rubbers which all exhibited a reduced change in elongation before and after heating at 190° C. for 504 hours, and had high heat aging resistance under a high temperature environment at 190° C. Among these, in the case where a combination of the diarylamine-based compound represented by General Formula (1) with the condensed heterocyclic compound represented by General Formula (19) was used as the antioxidant, the change in elongation before and after heating at 190° C. for 504 hours was further reduced, and higher heat aging resistance was exhibited.

In contrast, in the polymer compositions according to Comparative Examples 4 and 5 where an antioxidant other than the diarylamine-based compound represented by General Formula (1) was used as the antioxidant, the resulting cross-linked rubbers all exhibited a high change in elongation before and after heating at 190° C. for 504 hours, and had insufficient heat aging resistance under a high temperature environment at 190° C.

The invention claimed is:

1. A rubber composition comprising an acrylic rubber having a Mooney viscosity [ML1+4, 100° C.] of 10 to 80 and an antioxidant comprising a diarylamine-based compound represented by General Formula (1):

(1)

where, in General Formula (1), $A^1$ and $A^2$ each independently represent a $C_6$ to $C_{18}$ arylene group which may have a substituent, and $A^3$ and $A^4$ each independently represent an organic group having a cyclic imide structure which may have a substituent,
wherein a content of the antioxidant is 0.05 to 30 parts by weight relative to 100 parts by weight of the rubber.

2. The rubber composition according to claim 1, wherein $A^3$ and $A^4$ each independently are an organic group represented by General Formula (2) or (3):

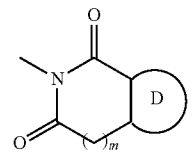
(2)

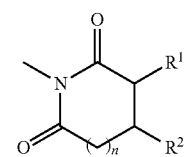
(3)

where, in General Formula (2), D represents a $C_6$ to $C_{18}$ ring which may have a substituent; "m" represents 0 or 1; in General Formula (3), $R^1$ and $R^2$ each independently represent a hydrogen atom, a $C_1$ to $C_{30}$ alkyl group which may have a substituent, or a $C_1$ to $C_{30}$ alkenyl group which may have a substituent; and "n" represents 0 or 1.

3. The rubber composition according to claim 2, wherein $A^3$ and $A^4$ each independently are any of organic groups represented by General Formulae (4) to (9):

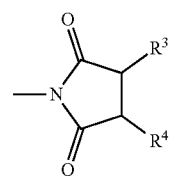
(4)

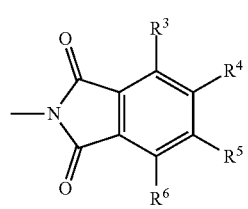
(5)

-continued

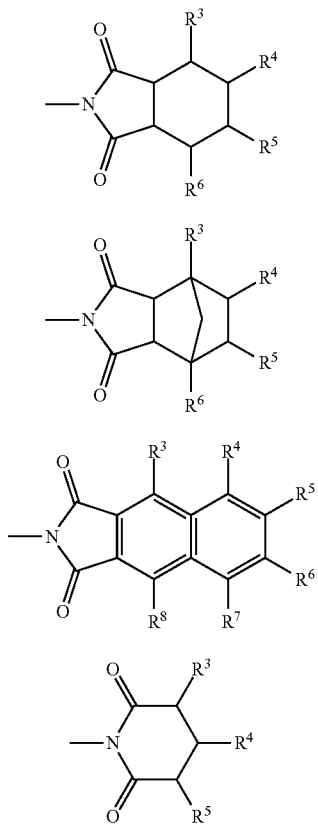

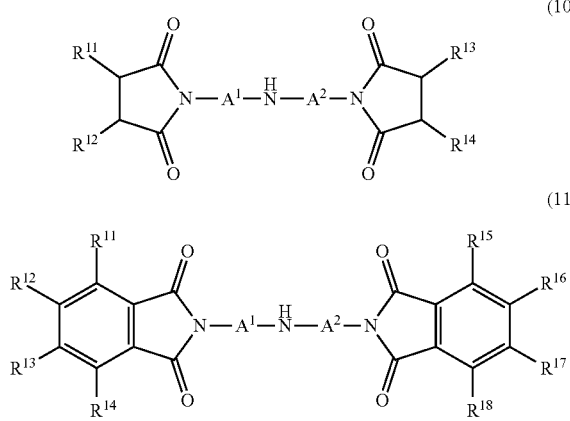

where, in General Formulae (4) to (9), $R^3$ to $R^8$ each independently represent a hydrogen atom, a $C_1$ to $C_{30}$ alkyl group, a $C_1$ to $C_{30}$ alkenyl group, —O—$R^9$, —O—C(=O)—$R^9$, —C(=O)—O—$R^9$, —C(=O)—NR$^9$(R$^{10}$), —NR$^9$—C(=O)—R$^{10}$, —CN, —SR$^9$, —S(=O)—R$^9$, or —S(=O)$_2$—R$^9$; $R^9$ and $R^{10}$ each independently represent a $C_1$ to $C_{30}$ alkyl group, a $C_1$ to $C_{30}$ alkenyl group, or a $C_6$ to $C_{12}$ aromatic group; and when two or more $R^3$ to $R^8$ are present, these may be the same or may be different.

4. The rubber composition according to claim 3, wherein the diarylamine-based compound is any of compounds represented by General Formulae (10) to (13):

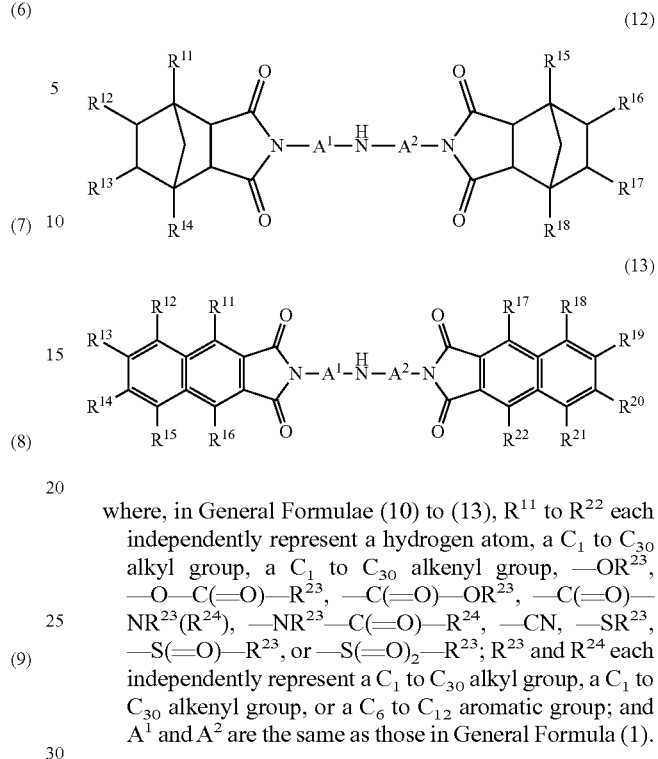

where, in General Formulae (10) to (13), $R^{11}$ to $R^{22}$ each independently represent a hydrogen atom, a $C_1$ to $C_{30}$ alkyl group, a $C_1$ to $C_{30}$ alkenyl group, —OR$^{23}$, —O—C(=O)—R$^{23}$, —C(=O)—OR$^{23}$, —C(=O)—NR$^{23}$(R$^{24}$), —NR$^{23}$—C(=O)—R$^{24}$, —CN, —SR$^{23}$, —S(=O)—R$^{23}$, or —S(=O)$_2$—R$^{23}$; $R^{23}$ and $R^{24}$ each independently represent a $C_1$ to $C_{30}$ alkyl group, a $C_1$ to $C_{30}$ alkenyl group, or a $C_6$ to $C_{12}$ aromatic group; and $A^1$ and $A^2$ are the same as those in General Formula (1).

5. The rubber composition according to claim 1, wherein $A^1$ and $A^2$ are a 1,4-phenylene group.

6. The rubber composition according to claim 1, wherein the diarylamine-based compound is any of compounds represented by General Formulae (14) to (18):

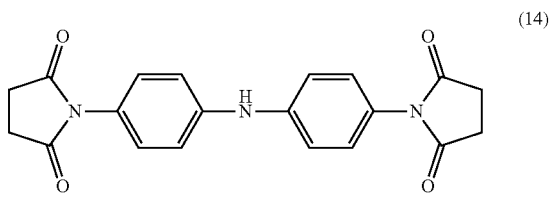

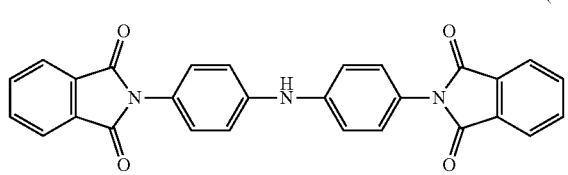

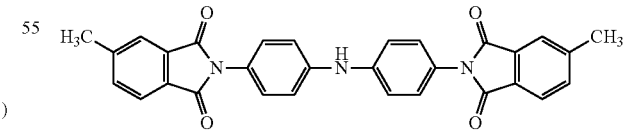

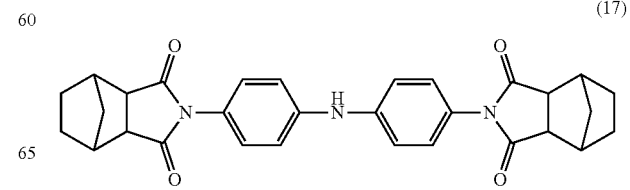

-continued

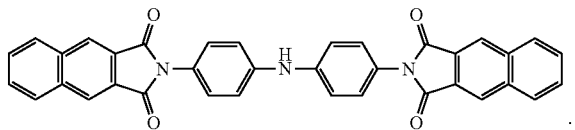
(18)

7. The rubber composition according to claim 1 further comprising a condensed heterocyclic compound represented by General Formula (19):

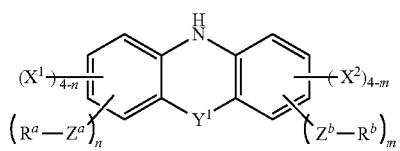
(19)

where, in the formula, $Y^1$ represents a chemical single bond, —S(=O)—, or —SO$_2$—;

$R^a$ and $R^b$ each independently represent a $C_1$ to $C_{30}$ organic group which may have a substituent;

$Z^a$ and $Z^b$ each independently represent a chemical single bond or —SO$_2$—;

$X^1$ and $X^2$ each independently represent a hydrogen atom, a halogen atom, a $C_1$ to $C_{10}$ alkyl group which may have a substituent, a cyano group, a nitro group, —OR$^{25}$, —O—C(=O)—R$^{25}$, —C(=O)—OR$^{25}$, —O—C(=O)—OR$^{25}$, —NR$^{26}$(R$^{27}$), —NR$^{26}$—C(=O)—R$^{25}$, —C(=O)—NR$^{26}$(R$^{27}$), or —O—C(=O)—NR$^{26}$(R$^{27}$), where R$^{25}$, R$^{26}$ and R$^{27}$ each independently represent a hydrogen atom or a $C_1$ to $C_{20}$ organic group which may have a substituent;

"n" and "m" each independently represent an integer of 0 to 2, and one of "n" and "m" is not 0; and when "n" and/or "m" is 2, two $R^a$ and two $R^b$ each may be the same or different.

8. The rubber composition according to claim 7, wherein $R^a$ and $R^b$ each independently represent a linear or branched $C_1$ to $C_{20}$ alkyl group which may have a substituent, or a phenyl group which may have a substituent.

9. The rubber composition according to claim 7, wherein the condensed heterocyclic compound represented by General Formula (19) is a compound represented by General Formula (20) or (21):

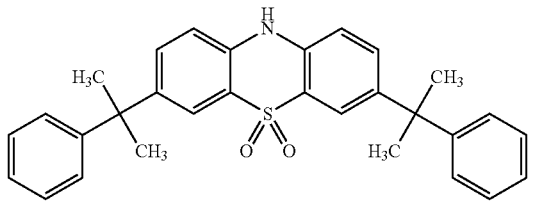
(20)

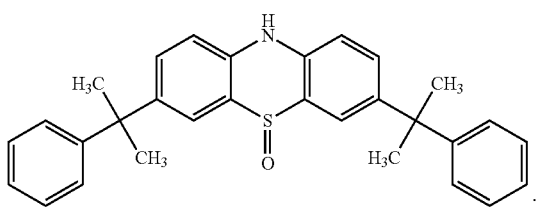
(21)

10. The rubber composition according to claim 7, wherein a weight ratio of the diarylamine-based compound to the condensed heterocyclic compound is 30:1 to 1:30 as "diarylamine-based compound: condensed heterocyclic compound".

11. The rubber composition according to claim 3, wherein in General Formula (4), $R^3$ and $R^4$ each represent a hydrogen atom, in General Formulae (5), (6), (8) and (9), $R^3$ to $R^8$ each independently represent a hydrogen atom, a $C_1$ to $C_{30}$ alkyl group, a $C_1$ to $C_{30}$ alkenyl group, —O—R$^9$, —O—C(=O)—R$^9$, —C(=O)—O—R$^9$, —C(=O)—NR$^9$(R$^{10}$), NR$^9$—C(=O)—R$^{10}$, —CN, —SR$^9$, —S—(=O)—R$^9$, or —S(=O)$_2$—R$^9$; R$^9$ and R$^{10}$ each independently represent a $C_1$ to $C_{30}$ alkyl group, a $C_1$ to $C_{30}$ alkenyl group, or a $C_6$ to $C_{12}$ aromatic group, in General Formula (7), $R^3$ to $R^6$ each represent a hydrogen atom; and when two or more $R^3$ to $R^8$ are present, these may be the same or may be different.

* * * * *